United States Patent
Smits et al.

(10) Patent No.: US 11,421,256 B2
(45) Date of Patent: Aug. 23, 2022

(54) PROCESS FOR ENZYMATIC HYDROLYSIS OF LIGNOCELLULOSIC MATERIAL AND FERMENTATION OF SUGARS

(71) Applicant: DSM IP ASSETS B.V., Heerlen (NL)

(72) Inventors: Johannes Petrus Smits, Echt (NL); Elisabeth Maria Gierveld, Echt (NL); Fop Van Der Hor, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 142 days.

(21) Appl. No.: 16/163,196

(22) Filed: Oct. 17, 2018

(65) Prior Publication Data
US 2019/0093137 A1 Mar. 28, 2019

Related U.S. Application Data

(63) Continuation of application No. 13/498,800, filed as application No. PCT/EP2010/064830 on Oct. 5, 2010, now abandoned.

(30) Foreign Application Priority Data

Oct. 8, 2009 (EP) .................................. 09172586

(51) Int. Cl.
*C12P 7/00* (2006.01)
*C12P 19/02* (2006.01)
(Continued)

(52) U.S. Cl.
CPC .............. *C12P 19/02* (2013.01); *C12P 7/10* (2013.01); *C12P 19/14* (2013.01);
(Continued)

(58) Field of Classification Search
CPC .. C12P 19/02; C12P 19/14; C12P 7/10; Y02E 50/10; C12R 2001/865
See application file for complete search history.

(56) References Cited

U.S. PATENT DOCUMENTS

| 4,368,268 A | 1/1983 | Gong |
| 5,352,606 A | 10/1994 | Takano et al. |

(Continued)

FOREIGN PATENT DOCUMENTS

| AU | 2010305447 C1 | 4/2012 |
| AU | 2014277778 B2 | 1/2015 |

(Continued)

OTHER PUBLICATIONS

Brat et al., Environmental Microbiology, 75:2304-2311, published in Apr. 2009 (Year: 2009).*

(Continued)

*Primary Examiner* — Allison M Fox
*Assistant Examiner* — Qing Xu
(74) *Attorney, Agent, or Firm* — McBee Moore & Vanik IP, LLC; Susan McBee; Chester Moore

(57) ABSTRACT

The invention relates to a process for the preparation of a fermentation product from ligno-cellulosic material, comprising the following steps:

a) optionally pre-treatment
b) optionally washing;
c) enzymatic hydrolysis;
d) fermentation; and
e) optionally recovery of a fermentation product;

wherein in step c) an enzyme composition is used that has a temperature optimum of 55 degrees C. or more, the hydrolysis time is 40 hours or more and the temperature is 50 degrees C. or more.

18 Claims, 10 Drawing Sheets

(51) Int. Cl.
  *C12P 7/10* (2006.01)
  *C12P 19/14* (2006.01)
  *C12R 1/645* (2006.01)
  *C12R 1/865* (2006.01)

(52) U.S. Cl.
  CPC .. *C12R 2001/645* (2021.05); *C12R 2001/865* (2021.05); *Y02E 50/10* (2013.01)

(56) References Cited

U.S. PATENT DOCUMENTS

| | | | |
|---|---|---|---|
| 5,487,989 A | | 1/1996 | Fowler et al. |
| 5,554,520 A | | 9/1996 | Fowler et al. |
| 6,475,768 B1 | * | 11/2002 | Otero ............... C12N 9/92 435/161 |
| 9,303,253 B2 | | 4/2016 | Van Maris et al. |
| 9,441,214 B2 | | 9/2016 | Schoonneveld-Bergmans et al. |
| 2002/0164730 A1 | | 11/2002 | Ballesteros Perdices et al. |
| 2005/0153411 A1 | * | 7/2005 | Wahlbom ............. C12N 1/18 435/161 |
| 2008/0138862 A1 | | 6/2008 | Felby et al. |
| 2009/0042266 A1 | | 2/2009 | Vehmaanpera et al. |
| 2009/0061490 A1 | | 3/2009 | Edwards et al. |
| 2009/0061495 A1 | | 3/2009 | Beatty et al. |
| 2010/0086965 A1 | | 4/2010 | Van Maris et al. |
| 2010/0151548 A1 | * | 6/2010 | Boles ............... C12N 15/81 435/161 |
| 2011/0143402 A1 | | 6/2011 | De Laat et al. |
| 2012/0114797 A1 | | 5/2012 | Perkins et al. |
| 2012/0183993 A1 | | 7/2012 | Smits et al. |
| 2019/0093137 A1 | | 3/2019 | Smits et al. |

FOREIGN PATENT DOCUMENTS

| | | | |
|---|---|---|---|
| CA | 2114265 A1 | | 7/1994 |
| EP | 2486139 A2 | | 8/2012 |
| EP | 3409782 A1 | | 12/2018 |
| WO | 2006/056838 A1 | | 6/2006 |
| WO | 2007/071818 | | 6/2007 |
| WO | 2007/091231 A1 | | 8/2007 |
| WO | 2008/041840 A1 | | 4/2008 |
| WO | 2008/150983 A1 | | 12/2008 |
| WO | 2009121058 A1 | | 10/2009 |
| WO | 2010/018105 | | 2/2010 |
| WO | WO-2011/131667 A | * | 4/2010 |
| WO | 2011/000949 A1 | | 1/2011 |
| WO | 2011/042437 A3 | | 4/2011 |
| WO | 2012/000890 A1 | | 1/2012 |

OTHER PUBLICATIONS

International Search Report for PCT/EP2010/064830 dated Nov. 7, 2011.
Harnpicharnchai et al., "Thermotolerant β-glcosidase Isolated from an Endophytic Fungi, *Periconia* SP., With a Possible Use for Biomass Conversion to Sugars", Protein Expression and Purification, vol. 67, No. 2, pp. 61-69 (Oct. 2, 2009).
Margot et al., "New Improvements for Lignosellulosic Ethanol", Current Opinion in Biotechnology, vol. 20, No. 3, pp. 372-380, (Jun. 3, 2009).
Exhibit TV-7/Jorgensen et al., "Liquefaction of Lignocellulose at High-Solids Concentrations", Biotechnology and Bioengineering, 96(05), Apr. 1, 2007.
Exhibit TV-4/Viikari et al., "Thermostable Enzymes in Lignocellulose Hydrolysis", Adv Biochem Engin/Biotechnol (2007) 108: 121-145.
Cara et al., "influence of solid loading on enzymatic hydrolysis of steam exploded or liquid hot water pretreated olive tree biomass", Process Biochemistry 42 (2007) p. 1003-1009.
Maheshwari et a., "Thermophilic Fungi: Their Physiology and Enzymes", Microbiology and Molecular Biology Reviews, 64(3) Sep. 2000, p. 461-488.
Exhibit TV-11/Dashtban et al., "Fungal Bioconversion of Lignocellulosic Residues; Opportunities & Perspectives", International Journal of Biological Sciences, 5(6) 2009, p. 578-595.
Mousdale et al., "Biofuels: Biotechnology, Chemistry, and Sustainable Development", CRC Press Taylor & Francis Group (2008) p. 66-118.
El-Mansi et al., "Fermentation Microbiology and Biotechnology", Second Edition, CRC Press Taylor & Francis Group (2007) p. 268-273.
Modenbach et al., "Enzymatic hydrolysis of biomass at high-solids loadings—A Review", Biomass and Bioenergy 56 (2013) 526-244.
Ioelovich et al., "Study of Enzymatic Hydrolysis of Pretreated Biomass at Increased Solids Loading", Peer-Reviewed Article, "High-solids hydrolysis", BioResources 7(4) (2012) 4672-4682.
Hodge et al., "Soluble and insoluble solids contributions to high-solids enzymatic hydrolysis of lignocellulose", Bioresource Technology 99 (2008) 8940-8948.
Kristensen et al., "Yield-determining factors in high-solids enzymatic hydrolysis of lignocellulose", Biotechnology for Biofuels 2(11) (2009) 1-10.
Mohagheghi et al., "High Solids Simultaneous Saccharification and Fermentation of Pretreated Wheat Straw to Ethanol", Applied Biochemistry and Biotechnology 33(1992) 67-81.
Exhibit TV-9/Varga et al., "High Solid Simultaneous Saccarification and Fermentation of Wet Oxidized Corn Stover to Ethanol", Biotechnology and Bioengineering 88(5) (2004) 567-574.
Karhumaa et al., "High activity of xylose reductase and xylitol dehydrogenase improves xylose fermentation by recombinant *Saccharomyces cerevisiae*", Appl Microbiol Biotechnol, 73: 1039-1046, 2007.
Australian Commissioner of Patents, "Notice of Opposition on Australian Patent Application No. 2010305447 in the Name of: DSM IP Assets B.V.- and -Oppposition thereto by: Novozymes North America, Inc." Jan. 2, 2015.
Australian Commissioner of Patents, "Statement of Grounds and Particulars in the matter of Australian Patent Application No. 2010305447 in the Name of: DSM IP Assets B.V.- and -Oppposition thereto by: Novozymes North America, Inc." Apr. 2, 2015.
Exhibit TV-1: Cv: Tony Vancov. Signed Jun. 30, 2015.
Exhibit TV-2: CV: Tony Vancov. Signed Jun. 30, 2015. Federal Court of Australia Practice Note CM 7 Expert Witnesses in Proceedings in the Federal Court of Australia. J L B Allsop Chief Justice Jun. 4, 2013.
Exhibit TV-3: Web of Science [5.17]—Export Transfer Service, Jun. 4, 2015.
Exhibit TV-12/Maris et al., "Development of Efficient Xylose Fermentation in *Saccharoryces cerevisiae*: Xylose Isomerase as a Key Component." Adv Biochem Engin/Biotechnol 108(2007) 179-204.
Exhibit TV-13/Maris et ai., "Development of Efficient Xylose Fermentation in *Saccharomyces cerevisiae*: Xylose Isomerase as a Key Component." Adv Biochem Engin/Biotechnol 108(2007) 179-204. Handwritten notes.
Exhibit TV-14: DSM IP Assets B.V.: European Patent Application 09172586.1/EP09172586, "Process for Enzymatic Hydrolysis of Lignocellulosic Material and Fermentation of Sugars," dated Aug. 10, 2009.
Exhibit TV-15/Chung et al., "Enzymatic Saccharification and Fermentation of Xylose-Optimized Dilute Acid-Treated Lignocellulosics." Applied Biochemistry and Biotechnology, vols. 121-124 (2005) 948-962.
Exhibit TV-16/Lu et al., "Cellulase Adsorption and an Evaluation of Enzyme Recycle During Hydrolysis of Steam-Exploded Softwood Residues." Applied Biochemistry and Biotechnology, vols. 98-100 (2002) 642-655.
Exhibit TV-17/Ramos et al., "The use of enzyme recycling and the influence of sugar accumulation on cellulose hydrolysis by Trichoderma cellulases." Enzyme Microb. Technol., 15(1993) 19-25.
Exhibit TV-18/Tu et al., "Recycling Cellulases during the Hydrolysis of Steam Exploded and Ethanol Pretreated Lodgepole Pine." Biotechnol. Prog. 23(2007) 1130-1137.
News Release by Shell International Media Office Shell First to Sell Gasoline Blended with Advanced Biofuel. Oct. 6, 20009.

(56) References Cited

OTHER PUBLICATIONS

O'Hara, "Towards a commercial lignocellulosic ethanol industry in Australia The Mackay Renewable Biocommodities Pilot Plant." 31st Annual Australian Society of Sugar Cane Technologists Conference 2009 (ASSCT 2009). Balina, New South Wales, Australia May 5-8, 2009.
Galbe et al., "Process Engineering Economics of Bioethanol Production." 108 Advances in Biochemical Engineering/Biotechnology Series. Adv Biochem Engin/Biotechnol (2007) 108: 303-327.
Summary of a Two Stage hydrolysis assay by Tony Vancov.
Declaration of Kelly Reynolds, signed Apr. 10, 2016, in the matter of Australian Patent Application 2010305447.
Declaration of Tony Vancov, signed Apr. 11, 2016, in the matter of Australian Patent Application 2010305447 and Exhibits TV-20-23.
Brodeur, Gary, et al., "Chemical and Physicochemical Pretreatment of Lignocellulosic Biomass: a Review", SAGE-Hindawi Access to Research, Enzyme Research, vol. 2011, Article ID 787532, 17 pages, Mar. 18, 2011.
Harmsen, P.F.H., et al. "Literature Review of Physical and Chemical Pretreatment Processes for Lignocellulosic Biomass", Food & Biobased Research, Energy Research Centre of the Netherlands, pp. 1-49, Sep. 2010.
Jacquet, N., et al. "Application of Steam Explosion as Pretreatment of Lignocellulosic Material: a Review", Industrial & Engineering Chemistry Research, American Chemical Society, pp. 2593-2598, 2015.
Kent, Michael, "Advanced Biology", University Press, Oxford, pp. 44-45, 2000.
Kim et al., "Strain engineering of *Saccharomyces cerevisiae* for enhanced xylose metabolism." Biotechnology Advances 31 (2013) 851-861.
Kumar et al., "Methods for Pretreatment of Lignoceilulosic Biomass for Efficient Hydrolysis and Biofuel Production", Industrial & Engineering Chemistry Research, Mar. 20, 2009. Downloaded from pubs.acs.org on Mar. 26, 2009.
Hahn-Hägerdal, Bärbel et al., "Towards industrial pentose-fermenting yeast strains", Applied Microbiology and Biotechnology, Apr. 2007, pp. 937-953, vol. 74, No. 5.
Lu, Yifeng et al., "Influence of High Solid Concentration on Enzymatic Hydrolysis and Fermentation of Steam-Exploded Corn Stover Biomass", Applied Microbiology and Biotechnology, 2010, pp. 360-369, vol. 160.
Summary of Applicant's Submission in opposition to Australian Patent Application No. 2010305447 dated Oct. 25, 2017.
Outline of Opponent's Submissions in opposition to Australian Patent Application No. 2010305447.
Statement of Grounds and Particulars, Marked copy, in opposition to Australian Patent Application No. 2010305447 dated Mar. 29, 2017.
Statement of Grounds and Particulars, Clean copy, in opposition to Australian Patent Application No. 2010305447 dated Mar. 29, 2017.
Summary of Applicant's Submission in opposition to Australian Patent Application No. 2010305447 dated Aug. 8, 2018.
Response within Administrative Nullity Level (with English translation) of Patent No. BR 1220160043703 dated Oct. 5, 2010.
Dashtban, Mehdi et al., "Fungal Bioconversion of Lignocellulosic Residues: Opportunities & Perspectives," International Journal of Biological Sciences, 2009, pp. 578-595, vol. 5, No. 6.
Power, Ronan F., "Enzymatic conversion of starch of fermentable sugars", The Alcohol Textbook, 4th Edition, Chapter 3, 2003, pp. 23-24, Nottingham University Press, Nottingham, United Kingdom.
Abbas, Charles A,, "Lignocellulosics to ethanol: meeting ethanol demand in the future", The Alcohol Textbook, 4th Edition, Chapter 5, 2003, pp. 41-57, Nottingham University Press, Nottingham, United Kingdom.
Technical Subsidies, Federal Public Service Ministry of Economics National Institute of Industrial Property for Brazilian Application No. 1220160043703 dated Aug. 28, 2020.
General coordination of appeals and administrative nullity processes, Federal Public Service Ministry of Economics National Institute of Industrial Property for Brazilian Application No. 1220160043703 dated Aug. 30, 2020.
Technical Report with English Translation, Federal Public Service Ministry of Economics National Institute of Industrial Property for Brazilian Application No. 1220160043703 dated Nov. 28, 2019.
Viikari, Liisa et al., "Thermostable enzymes in lignocellulose hydrolysis," Advances in Biochemcial Engineering/Biotechnology, 2007, pp. 121-145, vol. 108.
Auxiliary Request # 1 accompanying the response to Notice of Opposition in EP10768708.9, filed Nov. 9, 2021, 3 pages.
Auxiliary Request # 2 accompanying the response to Notice of Opposition in EP10768708.9, filed Nov. 9, 2021, 3 pages.
Electronic Acknowledgement of receipt from the response to Notice of Opposition filed in EP10768708.9 on Nov. 9, 2021, 2 pages.
Response to Notice of Opposition filed in EP10768708.9 on Nov. 9, 2021, 16 pages.
Communication of a Notice of Opposition received in EP10768708.9 dated Jun. 21, 2021, 29 pages.

\* cited by examiner

PROCESS FOR ENZYMATIC HYDROLYSIS OF LIGNOCELLULOSIC MATERIAL AND FERMENTATION OF SUGARS

CROSS-REFERENCE TO RELATED APPLICATIONS

This application is continuation of Ser. No. 13/498,800, filed 28 Mar. 2012, which is a § 371 National Stage Application of PCT/EP2010/064830, filed Oct. 5, 2010, which claims priority to European Application No. 9172586.1, filed Oct. 8, 2009. The disclosures of the priority applications are incorporated in their entirety herein by reference.

STATEMENT OF FEDERALLY SPONSORED RESEARCH AND DEVELOPMENT

This Invention was made with U.S. Government support under Contract No. DE-FG36-08G018079 awarded by the Department of Energy. The Government has certain rights in this invention.

BACKGROUND OF THE INVENTION

Field of the Invention

The invention relates to a process for the enzymatic hydrolysis of lignocellulosic material and fermentation of sugars.

Ligno-cellulosic plant material, herein also called feedstock, is a renewable source of energy in the form of sugars that can be converted into valuable products e.g. bio-fuel, such as bio-ethanol. During this process, (ligno or hemi)-cellulose present in the feedstock, such as wheat straw, corn stover, rice hulls, etc., is converted into reducing sugars by (hemi)-cellulolytic enzymes, which then are converted into valuable products such as ethanol by microorganisms like yeast, bacteria and fungi.

Since the (hemi)-cellulose is crystalline and entrapped in a network of lignin, the conversion into reducing sugars is in general slow and incomplete. Typically, enzymatic hydrolysis of untreated feedstock yields sugars <20% of theoretical quantity. By applying a chemical and thermo-physical pre-treatment, the (hemi)-cellulose is more accessible for the (hemi)-cellulolytic enzymes, and thus conversions go faster and at higher yields.

A typical ethanol yield from glucose, derived from pre-treated corn stover, is 40 gallons of ethanol per 1000 kg of dry corn stover [1], or 0.3 g ethanol per g feedstock. The maximum yield of ethanol on cellulose base is approximately 90%.

Cellulolytic enzymes—most of them are produced by species like *Trichoderma, Humicola* and *Aspergillus*—are commercially used to convert pre-treated feedstock into a mash containing insoluble (hemi)cellulose, reducing sugars made thereof, and lignin. This mash is then used in a fermentation during which the reducing sugars are converted into yeast biomass (cells), carbon dioxide and ethanol. The ethanol produced in this way is called bio-ethanol.

The common production of sugars from pre-treated ligno-celullosic feedstock, the hydrolysis also called liquefaction, pre-saccharification or saccharification, typically takes place during a process lasting 6-168 hours [2][4] under elevated temperatures of 45-50° C. [2] and non-sterile conditions. During this hydrolysis, the cellulose present is partly (typically 30-95%, dependable on enzyme activity and hydrolysis conditions) converted into reducing sugars. In case of inhibition of enzymes by compounds present in the pre-treated feedstock and by released sugars; and to minimize thermal inactivation, this period of elevated temperature is minimized as much as possible.

The fermentation following the hydrolysis takes place in a separate anaerobic process step, either in the same or in a different vessel, in which temperature is adjusted to 30-33° C. (mesophilic process) to accommodate growth and ethanol production by microbial biomass, commonly yeasts. During this fermentation process, the remaining (hemi)cellulosic material is converted into reducing sugars by the enzymes already present from the hydrolysis step, while microbial biomass and ethanol are produced. This type of fermentation is therefore often called Simultaneously Saccharification and Fermentation, SSF. The fermentation is finished once (hemi) cellulosic material is converted into fermentable sugars and all fermentable sugars are converted into ethanol, carbon dioxide and microbial cells. This may take up to 6 days. The overall process time of hydrolysis and fermentation thus may amount up to 7 days.

The so obtained fermented mash consists of non-fermentable sugars, non-hydrolysable (hemi) cellulosic material, lignin, microbial cells (most common yeast cells), water, ethanol, dissolved carbon dioxide. During the successive steps, ethanol is distilled from the mash and further purified. The remaining solid suspension is dried and used as, for instance, burning fuel, fertilizer or cattle feed.

With each batch of feedstock, enzymes are added to maximize the yield and rate of fermentable sugars released from the pre-treated ligno-cellulosic feedstock during the given process time. In general, costs for enzymes production, feedstock to ethanol yields and investments are major cost factors in the overall production costs [2]. Thus far, cost of enzyme usage reduction is achieved by applying enzyme products from a single or from multiple microbial sources [7] with broader and/or higher (specific) hydrolytic activity which use aims at a lower enzyme need, faster conversion rates and/or a higher conversion yields, and thus at overall lower bio-ethanol production costs. This requires large investments in research and development of these enzyme products. In case of an enzyme product composed of enzymes from multiple microbial sources, large capital investments are needed for production of each single enzyme compound.

It is therefore desirable to improve the above process involving hydrolysis and fermentation.

Thermostable cellulolytic enzymes derived from *Talaromyces*, have been used for degrading ligno-cellulosic feedstock and these enzymes are known for their thermostability in WO2007091231 [3]. However, no disclosure is given how to optimize the process of hydrolysis and fermentation.

SUMMARY OF THE INVENTION

An object of the invention is therefore to provide a process in which the hydrolysis step and fermentation step are conducted at optimal temperature conditions. Another object of the invention is to provide a process involving hydrolysis and fermentation having a reduced process time. Further object of the invention is to provide a process, wherein the dosage of enzyme may be reduced and at the same time output of useful fermentation product is maintained at the same level. Another object is to provide a process wherein risk of contamination by contaminating microorganisms, is reduced. Another object is to provide a process wherein the dry-matter content is increased. Another object is to provide a process involving hydrolysis and fermentation, wherein the process conditions of the fermentation are optimized. One or more of these objects are attained according to the invention. The present invention provides a process for the preparation of a fermentation product from ligno-cellulosic material, comprising the following steps:

a) optionally pre-treatment
b) optionally washing;
c) enzymatic hydrolysis;
d) fermentation; and
e) optionally recovery of a fermentation product;
wherein in step c) an enzyme composition is used that has a temperature optimum of 55 degrees C. or more, the hydrolysis time is 40 hours or more and the hydrolysis temperature is 50 degrees C. or more.

Surprisingly, according to the invention, by the provision of an enzyme composition that is stable and has a temperature optimum of 55 degrees C. or more for the enzymatic hydrolysis step c), it is possible to attain many process advantages, including optimal temperature conditions, reduced process time, reduced dosage of enzyme, reduced risk of contamination, higher dry-matter concentrations, re-use of enzymes and other process optimizations, resulting in reduced costs.

In one embodiment of this process, the fermentation time is 18-120 hours. In an embodiment the stable enzyme composition used retains activity for 30 hours or more. According to a further embodiment the hydrolysis is conducted at a temperature of 55° C. or more. In a preferred embodiment, the enzyme composition is derived from a microorganism of genus *Talaromyces*. The process of the invention will be illustrated in more detail below.

DETAILED DESCRIPTION OF THE INVENTION

Figure 1:
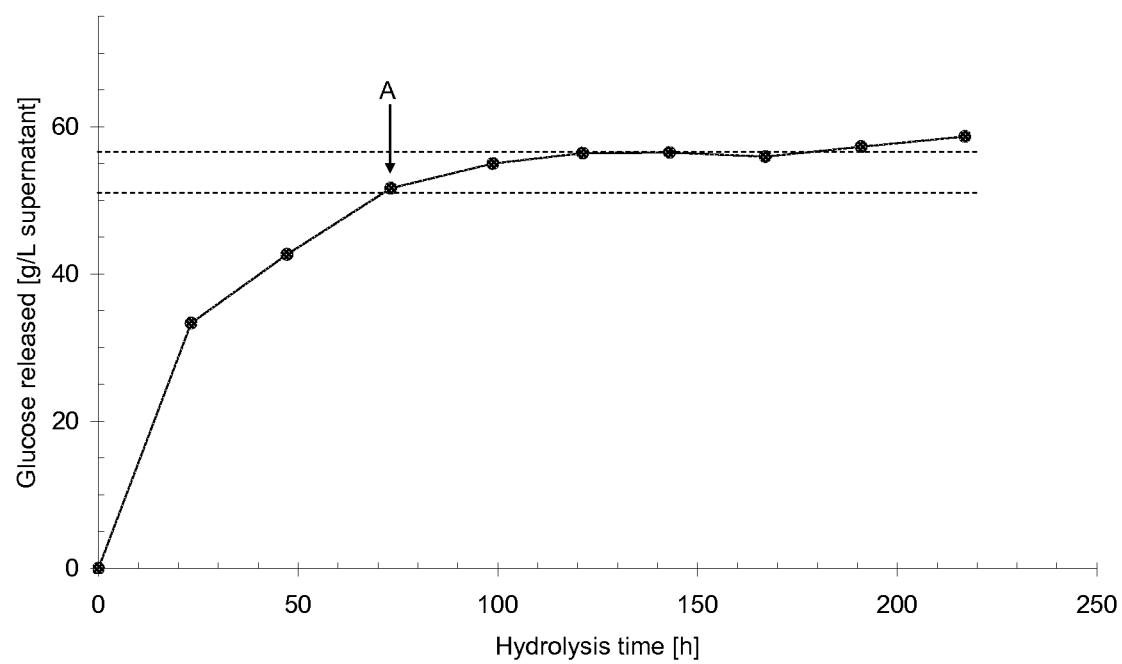
FIG. 1: The release in time of glucose from a 10% dry-matter suspension of feed stock using stable cellulolytic *Talaromyces* enzymes. The upper dotted line indicates the theoretically maximum of glucose that can be released, based on the cellulose composition of the feedstock. The lower dotted line indicates the 90% conversion level. A indicates the moment the 90% level is achieved.

The invention is now described in all its embodiments, in more detail.

Stable Enzyme Composition

According to the invention, in the hydrolysis step, a stable enzyme composition is used, that has a temperature optimum of 55 degrees C. or more, preferably of 60 degrees C. or more, or of 65 degrees or more. Temperature optimum is determined by measuring activity of the enzyme composition at different temperatures and plotting the activity against temperature, and then determining the optimum temperature i.e the temperature at which the highest activity is found.

Stable enzyme composition herein means that the enzyme composition retains activity after 30 hours of hydrolysis reaction time, preferably at least 10%, 20%, 30%, 40%, 50%, 60%, 65%, 70%, 75%, 80% 85%, 90%, 95%, 96%, 97%, 98%, 99% or 100% of its initial activity after 30 hours of hydrolysis reaction time. Preferably the enzyme composition retains activity after 40, 50, 60, 70, 80, 90 100, 150, 200, 250, 300, 350, 400, 450, 500 hours of hydrolysis reaction time.

The enzyme composition may be derived from a microorganism. A composition for use in a process of the invention will comprise enzymatic activities typically derived from a saprophyte fungal microorganism of the class *Penicillium* and from the genus *Talaromyces*, for example *Talaromyces emersonii*. *Talaromyces emersonii* may also be referred to as *Geosmithia emersonii* or *Penicillium emersonii*. *Talaromyces emersonii* has also been referred to as *Talaromyces duponti* and *Penicillium duponti*.

The enzyme composition may be prepared by fermentation of a suitable substrate with the microorganism, e.g. *Talaromyces emersonii*, wherein the enzyme composition is produced by the microorganism. Optionally a substrate is used that induces the expression of the enzymes in the enzyme composition.

The enzyme composition is used to release sugars from lignocellulose, that comprises polysaccharides. The major polysaccharides are cellulose (glucans), hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucoronic acid and other hexoses and pentoses occurs under the action of different enzymes acting in concert.

In addition, pectins and other pectic substances such as arabinans may make up considerably proportion of the dry mass of typically cell walls from non-woody plant tissues (about a quarter to half of dry mass may be pectins).

Cellulose is a linear polysaccharide composed of glucose residues linked by β-1,4 bonds. The linear nature of the cellulose fibers, as well as the stoichiometry of the β-linked glucose (relative to α) generates structures more prone to interstrand hydrogen bonding than the highly branched α-linked structures of starch. Thus, cellulose polymers are generally less soluble, and form more tightly bound fibers than the fibers found in starch.

Enzymes that may be included in the stable enzyme composition used in the invention are now described in more detail:

Endoglucanases (EG) and exo-cellobiohydrolases (CBH) catalyze the hydrolysis of insoluble cellulose to cellooligosaccharides (cellobiose as a main product), while β-glucosidases (BG) convert the oligosaccharides, mainly cellobiose and cellotriose to glucose.

Hemicellulose is a complex polymer, and its composition often varies widely from organism to organism, and from one tissue type to another. In general, a main component of hemicellulose is β-1,4-linked xylose, a five carbon sugar. However, this xylose is often branched at 0-3 and/or 0-2 atom of xylose, and can be substituted with linkages to arabinose, galactose, mannose, glucuronic acid, galacturonic acid or by esterification to acetic acid (and esterification of ferulic acid to arabinose). Hemicellulose can also contain glucan, which is a general term for β-linked six carbon sugars (such as the β-(1,3)(1,4) glucans and heteroglucans mentioned previously) and additionally glucomannans (in which both glucose and mannose are present in the linear backbone, linked to each other by β-linkages).

Xylanases together with other accessory enzymes, for example α-L-arabinofuranosidases, feruloyl and acetylxylan esterases, glucuronidases, and β-xylosidases) catalyze the hydrolysis of hemicelluloses.

Pectic substances include pectins, arabinans, galactans and arabinogalactans. Pectins are the most complex polysaccharides in the plant cell wall. They are built up around a core chain of α(1,4)-linked D-galacturonic acid units interspersed to some degree with L-rhamnose. In any one cell wall there are a number of structural units that fit this description and it has generally been considered that in a single pectic molecule, the core chains of different structural units are continuous with one another.

The principal types of structural unit are: galacturonan (homogalacturonan), which may be substituted with methanol on the carboxyl group and acetate on O-2 and O-3; rhamnogalacturonan I (RGI), in which galacturonic acid units alternate with rhamnose units carrying (1,4)-linked galactan and (1,5)-linked arabinan side-chains. The arabinan side-chains may be attached directly to rhamnose or indirectly through the galactan chains; xylogalacturonan, with single xylosyl units on O-3 of galacturonic acid (closely associated with RGI); and rhamnogalacturonan II (RGII), a particularly complex minor unit containing unusual sugars, for example apiose. An RGII unit may contain two apiosyl residues which, under suitable ionic conditions, can reversibly form esters with borate.

A composition for use in a method of the invention comprises at least two activities, although typically a composition will comprise more than two activities, for example, three, four, five, six, seven, eight, nine or more. Typically, a composition of the invention may comprise at least one cellulase and at least one hemicellulase. However, a composition of the invention may comprise cellulases, but no xylanases. In addition, a composition of the invention may comprise auxiliary enzyme activity, i.e. additional activity which, either directly or indirectly leads to lignocellulose degradation. Examples of such auxiliary activities are mentioned herein.

Thus, a composition for use in the invention may comprise endoglucanase activity and/or cellobiohydrolase activity and/or ß-glucosidase activity. A composition for use in the invention may comprise more than one enzyme activity in one or more of those classes. For example, a composition for use in the invention may comprise two endoglucanase activities, for example, endo-1,3(1,4)-β glucanase activity and endo-β-1,4-glucanase activity. Such a composition may also comprise one or more xylanase activities. Such a composition may comprise an auxiliary enzyme activity.

A composition for use in the invention may be derived from *Talaromyces emersonii*. In the invention, it is anticipated that a core set of (lignocellulose degrading) enzyme activities may be derived from *Talaromyces emersonii*. *Talaromyces emersonii* can provide a highly effective set of activities as demonstrated herein for the hydrolysis of lignocellulosic biomass. That activity can then be supplemented with additional enzyme activities from other sources. Such additional activities may be derived from classical sources and/or produced by a genetically modified organism.

The activities in a composition for use in the invention may be thermostable. Herein, this means that the activity has a temperature optimum of 40° C. or higher, for example about 50° C. or higher, such as about 60° C. or higher, for example about 70° C. or higher, such as about 75° C. or higher, for example about 80° C. or higher such as 85° C. or higher. Activities in a composition for use in the invention will typically not have the same temperature optima, but preferably will, nevertheless, be thermostable.

In addition, enzyme activities in a composition for use in the invention may be able to work at low pH. For the purposes of this invention, low pH indicates a pH of about 5.5 or lower, about 5 or lower, about 4.9 or lower, about 4.8 or lower, about 4.7 or lower, about 4,6 or lower, about 4.5 or lower, about 4.4 or lower, about 4.3 or lower, about 4.2 or lower, about 4,1 or lower, about 4.0 or lower about 3.9 or lower, or about 3.8 or lower, about 3.7 or lower, about 3.6 or lower, or about 3.5 or lower.

Activities in a composition for use in the invention may be defined by a combination of any of the above temperature optima and pH values.

The composition used in a method of the invention may comprise, in addition to the activities derived from *Talaromyces*, a cellulase (for example one derived from a source other than *Talaromyces*) and/or a hemicellulase (for example one derived from a source other than *Talaromyces*) and/or a pectinase.

A composition for use in the invention may comprise one, two, three, four classes or more of cellulase, for example one, two three or four or all of an endoglucanase (EG), one or two exo-cellobiohydrolase (CBH) and a β-glucosidase (BG). A composition for use in the invention may comprise two or more of any of these classes of cellulase.

The β-glucosidase enzyme native to *Talaromyces* is known to be very active, Vmax value for the *Talaromyces* β-glucosidase Cel3a is 512 IU/mg which is considerably higher than the values reported for the β-glucosidases from the other fungal sources (P. Murray et al./Protein Expression and PuriWcation 38 (2004) 248-257) Despite the high activity of the β-glucosidase in the compositions according to the invention, and the high glucose levels achieved, no glucose inhibition occurs. This is advantageous since high activities and high glucose levels may be combined using the compositions according to the invention.

A composition of the invention may comprise an activity which has a different type of cellulase activity and/or hemicellulase activity and/or pectinase activity than that provided by the composition for use in a method of the invention. For example, a composition of the invention may comprise one type of cellulase and/or hemicellulase activity and/or pectinase activity provided by a composition as described herein and a second type of cellulase and/or hemicellulase activity and/or pectinase activity provided by an additional cellulose/hemicellulase/pectinase.

Herein, a cellulase is any polypeptide which is capable of degrading or modifying cellulose. A polypeptide which is capable of degrading cellulose is one which is capable of catalysing the process of breaking down cellulose into smaller units, either partially, for example into cellodextrins, or completely into glucose monomers. A cellulase according to the invention may give rise to a mixed population of cellodextrins and glucose monomers when contacted with the cellulase. Such degradation will typically take place by way of a hydrolysis reaction.

Herein, a hemicellulase is any polypeptide which is capable of degrading or modifying hemicellulose. That is to say, a hemicellulase may be capable of degrading or modifying one or more of xylan, glucuronoxylan, arabinoxylan, glucomannan and xyloglucan. A polypeptide which is capable of degrading a hemicellulose is one which is capable of catalysing the process of breaking down the hemicellulose into smaller polysaccharides, either partially, for example into oligosaccharides, or completely into sugar monomers, for example hexose or pentose sugar monomers. A hemicellulase according to the invention may give rise to a mixed population of oligosaccharides and sugar monomers when contacted with the hemicellulase. Such degradation will typically take place by way of a hydrolysis reaction.

Herein, a pectinase is any polypeptide which is capable of degrading or modifying pectin. A polypeptide which is capable of degrading pectin is one which is capable of catalysing the process of breaking down pectin into smaller units, either partially, for example into oligosaccharides, or completely into sugar monomers. A pectinase according to the invention may give rise to a mixed population of oligosacchardies and sugar monomers when contacted with the pectinase. Such degradation will typically take place by way of a hydrolysis reaction.

Accordingly, a composition of the invention may comprise any cellulase, for example, a cellobiohydrolase, an endo-β-1,4-glucanase, a β-glucosidase or a β-(1,3)(1,4)-glucanase.

Herein, a cellobiohydrolase (EC 3.2.1.91) is any polypeptide which is capable of catalysing the hydrolysis of 1,4-β-D-glucosidic linkages in cellulose or cellotetraose, releasing cellobiose from the ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exocellobiohydrolase or exoglucanase.

Herein, an endo-β-1,4-glucanase (EC 3.2.1.4) is any polypeptide which is capable of catalysing the endohydrolysis of 1,4-β-D-glucosidic linkages in cellulose, lichenin or cereal β-D-glucans. Such a polypeptide may also be capable of hydrolyzing 1,4-linkages in β-D-glucans also containing 1,3-linkages. This enzyme may also be referred to as cellulase, avicelase, β-1,4-endoglucan hydrolase, β-1,4-glucanase, carboxymethyl cellulase, celludextrinase, endo-1,4-β-D-glucanase, endo-1,4-β-D-glucanohydrolase, endo-1,4-β-glucanase or endoglucanase.

Herein, a β-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalase, β-glucoside glucohydrolase, cellobiase or gentobiase.

Herein a β-(1,3)(1,4)-glucanase (EC 3.2.1.73) is any polypeptide which is capable of catalyzing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucanse when the glucose residue whose reducing group is involved in the linkage to be hydrolysed is itself substituted at C-3. Alternative names include endo-1,3-beta-glucanase, laminarinase, 1,3-(1,3;1,4)-beta-D-glucan 3 (4) glucanohydrolase; substrates include laminarin, lichenin and cereal beta-D-glucans.

A composition of the invention may comprise any hemicellulase, for example, an endoxylanase, a β-xylosidase, a α-L-arabionofuranosidase, an α-D-glucuronidase, an acetyl xylan esterase, a feruloyl esterase, a coumaroyl esterase, an α-galactosidase, a β-galactosidase, a β-mannanase or a β-mannosidase.

Herein, an endoxylanase (EC 3.2.1.8) is any polypeptide which is capable of catalyzing the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyse 1,4 xylosidic linkages in glucuronoarabinoxylans.

Herein, a β-xylosidase (EC 3.2.1.37) is any polypeptide which is capable of catalyzing the hydrolysis of 1.4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase.

Herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

Herein, an α-D-glucuronidase (EC 3.2.1.139) is any polypeptide which is capable of catalyzing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyse 4-O-methylated glucoronic acid, which can also be present as a substituent in xylans. Alternative is EC 3.2.1.131: xylan alpha-1,2-glucuronosidase, which catalyses the hydrolysis of alpha-1,2-(4-O-methyl)glucuronosyl links.

Herein, an acetyl xylan esterase (EC 3.1.1.72) is any polypeptide which is capable of catalyzing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin.

Herein, a feruloyl esterase (EC 3.1.1.73) is any polypeptide which is capable of catalyzing a reaction of the form: feruloyl-saccharide+H(2)O=ferulate+saccharide. The saccharide may be, for example, an oligosaccharide or a polysaccharide. It may typically catalyze the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin.

Herein, a coumaroyl esterase (EC 3.1.1.73) is any polypeptide which is capable of catalyzing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

Herein, an α-galactosidase (EC 3.2.1.22) is any polypeptide which is capable of catalyzing the hydrolysis of of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

Herein, a β-galactosidase (EC 3.2.1.23) is any polypeptide which is capable of catalyzing the hydrolysis of terminal non-reducing β-D-galactose residues in β-D-galactosides. Such a polypeptide may also be capable of hydrolyzing α-L-arabinosides. This enzyme may also be referred to as exo-(1→4)-β-D-galactanase or lactase.

Herein, a β-mannanase (EC 3.2.1.78) is any polypeptide which is capable of catalyzing the random hydrolysis of 1,4-β-D-mannosidic linkages in mannans, galactomannans and glucomannans. This enzyme may also be referred to as mannan endo-1,4-β-mannosidase or endo-1,4-mannanase.

Herein, a β-mannosidase (EC 3.2.1.25) is any polypeptide which is capable of catalyzing the hydrolysis of terminal, non-reducing β-D-mannose residues in β-D-mannosides. This enzyme may also be referred to as mannanase or mannase.

A composition of the invention may comprise any pectinase, for example an endo polygalacturonase, a pectin methyl esterase, an endo-galactanase, a beta galactosidase, a pectin acetyl esterase, an endo-pectin lyase, pectate lyase, alpha rhamnosidase, an exo-galacturonase, an expolygalacturonate lyase, a rhamnogalacturonan hydrolase, a rhamnogalacturonan lyase, a rhamnogalacturonan acetyl esterase, a rhamnogalacturonan galacturonohydrolase, a xylogalacturonase.

Herein, an endo-polygalacturonase (EC 3.2.1.15) is any polypeptide which is capable of catalyzing the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

Herein, a pectin methyl esterase (EC 3.1.1.11) is any enzyme which is capable of catalyzing the reaction: pectin+n H$_2$O=n methanol+pectate. The enzyme may also been known as pectinesterase, pectin demethoxylase, pectin methoxylase, pectin methylesterase, pectase, pectinoesterase or pectin pectylhydrolase.

Herein, an endo-galactanase (EC 3.2.1.89) is any enzyme capable of catalyzing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

Herein, a pectin acetyl esterase is defined herein as any enzyme which has an acetyl esterase activity which catalyzes the deacetylation of the acetyl groups at the hydroxyl groups of GalUA residues of pectin Herein, an endo-pectin lyase (EC 4.2.2.10) is any enzyme capable of catalyzing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

Herein, a pectate lyase (EC 4.2.2.2) is any enzyme capable of catalyzing the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

Herein, an alpha rhamnosidase (EC 3.2.1.40) is any polypeptide which is capable of catalyzing the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

Herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

Herein, exo-galacturonase (EC 3.2.1.67) is any polypeptide capable of catalyzing: (1,4-α-D-galacturonide)$_n$+H$_2$O=(1,4-α-D-galacturonide)$_{n-1}$+D-galacturonate. The enzyme may also be known as galacturan 1,4-α-galacturonidase, exopolygalacturonase, poly(galacturonate) hydrolase, exo- D-galacturonase, exo-D-galacturonanase, exopoly-D-galacturonase or poly(1,4-α-D-galacturonide) galacturonohydrolase.

Herein, exopolygalacturonate lyase (EC 4.2.2.9) is any polypeptide capable of catalyzing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

Herein, rhamnogalacturonan hydrolase is any polypeptide which is capable of hydrolyzing the linkage between galactosyluronic acid acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

Herein, rhamnogalacturonan lyase is any polypeptide which is any polypeptide which is capable of cleaving α-L-Rhap-(1→4)-α-D-GalpA linkages in an endo-fashion in rhamnogalacturonan by beta-elimination.

Herein, rhamnogalacturonan acetyl esterase is any polypeptide which catalyzes the deacetylation of the backbone of alternating rhamnose and galacturonic acid residues in rhamnogalacturonan.

Herein, rhamnogalacturonan galacturonohydrolase is any polypeptide which is capable of hydrolyzing galacturonic acid from the non-reducing end of strictly alternating rhamnogalacturonan structures in an exo-fashion.

Herein, xylogalacturonase is any polypeptide which acts on xylogalacturonan by cleaving the β-xylose substituted galacturonic acid backbone in an endo-manner. This enzyme may also be known as xylogalacturonan hydrolase.

Herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

Herein, endo-arabinanase (EC 3.2.1.99) is any polypeptide which is capable of catalyzing endohydrolysis of 1,5-α-arabinofuranosidic linkages in 1,5-arabinans. The enzyme may also be know as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

A composition of the invention will typically comprise at least one cellulase and/or at least one hemicellulase and/or at least one pectinase (one of which is a polypeptide according to the invention). A composition of the invention may comprise a cellobiohydrolase, an endoglucanase and/or a β-glucosidase. Such a composition may also comprise one or more hemicellulases and/or one or more pectinases.

In addition, one or more (for example two, three, four or all) of an amylase, a protease, a lipase, a ligninase, a hexosyltransferase, a glucuronidase or an expansin or a cellulose induced protein or a cellulose integrating protein or like protein may be present in a composition of the invention (these are referred to as auxiliary activities above).

"Protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the invention incorporated herein by reference. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phospoglycerides, lipoproteins, diacylglycerols, and the like. In plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.1.14), manganese peroxidases (EC 1.11.1.13), laccases (EC 1.10.3.2) and feruloyl esterases (EC 3.1.1.73).

"Hexosyltransferase" (2.4.1-) includes enzymes which are capable of catalyzing a transferase reaction, but which can also catalyze a hydrolysis reaction, for example of cellulose and/or cellulose degradation products. An example of a hexosyltransferase which may be used in the invention is a ß-glucanosyltransferase. Such an enzyme may be able to catalyze degradation of (1,3)(1,4)glucan and/or cellulose and/or a cellulose degradation product.

"Glucuronidase" includes enzymes that catalyze the hydrolysis of a glucoronoside, for example β-glucuronoside to yield an alcohol. Many glucuronidases have been characterized and may be suitable for use in the invention, for example β-glucuronidase (EC 3.2.1.31), hyalurono-glucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

A composition for use in the invention may comprise an expansin or expansin-like protein, such as a swollenin (see Salheimo et al., Eur. J. Biohem. 269, 4202-4211, 2002) or a swollenin-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this invention, an expansin-like protein or swollenin-like protein may comprise one or both of such domains and/or may disrupt the structure of cell walls (such as disrupting cellulose structure), optionally without producing detectable amounts of reducing sugars.

A composition for use in the invention may a cellulose induced protein, for example the polypeptide product of the cip1 or cip2 gene or similar genes (see Foreman et al., J. Biol. Chem. 278(34), 31988-31997, 2003), a cellulose/cellulosome integrating protein, for example the polypeptide product of the cipA or cipC gene, or a scaffoldin or a scaffoldin-like protein. Scaffoldins and cellulose integrating proteins are multi-functional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM)

that mediates attachment of the cellulosome to its substrate. A scaffoldin or cellulose integrating protein for the purposes of this invention may comprise one or both of such domains.

A composition for use in a method of the invention may be composed of a member of each of the classes of enzymes mentioned above, several members of one enzyme class, or any combination of these enzymes classes or helper proteins (i.e. those proteins mentioned herein which do not have enzymatic activity per se, but do nevertheless assist in lignocellulosic degradation).

A composition for use in a method of the invention may be composed of enzymes from (1) commercial suppliers; (2) cloned genes expressing enzymes; (3) complex broth (such as that resulting from growth of a microbial strain in media, wherein the strains secrete proteins and enzymes into the media; (4) cell lysates of strains grown as in (3); and/or (5) plant material expressing enzymes. Different enzymes in a composition of the invention may be obtained from different sources.

The enzymes can be produced either exogenously in microorganisms, yeasts, fungi, bacteria or plants, then isolated and added, for example, to lignocellulosic feedstock. Alternatively, the enzymes are produced, but not isolated, and crude cell mass fermentation broth, or plant material (such as corn stover or wheat straw), and the like may be added to, for example, the feedstock. Alternatively, the crude cell mass or enzyme production medium or plant material may be treated to prevent further microbial growth (for example, by heating or addition of antimicrobial agents), then added to, for example, a feedstock. These crude enzyme mixtures may include the organism producing the enzyme. Alternatively, the enzyme may be produced in a fermentation that uses (pre-treated) feedstock (such as corn stover or wheat straw) to provide nutrition to an organism that produces an enzyme(s). In this manner, plants that produce the enzymes may themselves serve as a lignocellulosic feedstock and be added into lignocellulosic feedstock.

In the uses and methods described herein, the components of the compositions described above may be provided concomitantly (i.e. as a single composition per se) or separately or sequentially.

The invention thus relates to methods in which the composition described above are used and to uses of the composition in industrial processes.

Ligno-Cellulosic Material

Lignocellulosic material herein includes any lignocellulosic and/or hemicellulosic material. Lignocellulosic material suitable for use as feedstock in the invention includes biomass, e.g. virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane bagasse, switch grass, miscanthus, corn, corn stover, corn husks, corn cobs, canola stems, soybean stems, sweet sorghum, corn kernel including fiber from kernels, products and by-products from milling of grains such as corn, wheat and barley (including wet milling and dry milling) often called "bran or fibre" as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforementioned singularly or in any combination or mixture thereof.

Pre-Treatment

The feedstock may optionally be pre-treated with heat, mechanical and/or chemical modification or any combination of such methods in order to to enhance the accessibility of the substrate to enzymatic hydrolysis and/or hydrolyse the hemicellulose and/or solubilize the hemicellulose and/or cellulose and/or lignin, in any way known in the art. In one embodiment, the pre-treatment is conducted treating the lignocellulose with steam explosion, hot water treatment or treatment with dilute acid or dilute base.

Washing Step

Optionally, the process according to the invention comprises a washing step. The optional washing step may be used to remove water soluble compounds that may act as inhibitors for the fermentation step. The washing step may be conducted in known manner.

Enzymatic Hydrolysis

The process according to the invention comprises an enzymatic hydrolysis step. The enzymatic hydrolysis includes, but is not limited to, hydrolysis for the purpose of liquification of the feedstock and hydrolysis for the purpose of releasing sugar from the feedstock or both. In this step optionally pre-treated and optionally washed ligno-cellulosic material is brought into contact with the enzyme composition according to the invention. Depending on the lignocellulosic material and the pre-treatment, the different reaction conditions, e.g. temperature, enzyme dosage, hydrolysis reaction time and dry matter concentration, may be adapted by the skilled person in order to achieve a desired conversion of lignocellulose to sugar. Some indications are given hereafter.

In one aspect of the invention the hydrolysis is conducted at a temperature of 50° C. or more, 55° C. or more, 60° C. or more, 65° C. or more, or 70° C. or more. The high temperature during hydrolysis has many advantages, which include working at the optimum temperature of the enzyme composition, the reduction of risk of (bacterial) contamination, reduced viscosity, smaller amount of cooling water required, use of cooling water with a higher temperature, re-use of the enzymes and more.

In a further aspect of the invention, the amount of enzyme composition added (herein also called enzyme dosage or enzyme load) is low. In an embodiment the amount of enzyme is 6 mg protein/g dry matter weight or lower, 5 mg protein/g dry matter or lower, 4 mg protein/g dry matter or lower, 3 mg protein/g dry matter or lower, 2 mg protein/g dry matter or lower, or 1 mg protein/g dry matter or lower (expressed as protein in mg protein/g dry matter). In an embodiment, the amount of enzyme is 0.5 mg enzyme/g dry matter weight or lower, 0.4 mg enzyme composition/g dry matter weight or lower, 0.3 mg enzyme/g dry matter weight or lower, 0.25 mg enzyme/g dry matter weight or lower, 0.20 mg enzyme/g dry matter weight or lower, 0.18 mg enzyme/g dry matter weight or lower, 0.15 mg enzyme/g dry matter weight or lower or 0.10 mg enzyme/g dry matter weight or lower (expressed as total of cellulase enzymes in mg enzyme/g dry matter). Low enzyme dosage is possible, since because of the activity and stability of the enzymes, it is possible to increase the hydrolysis reaction time.

In a further aspect of the invention, the hydrolysis reaction time is 40 hours or more, 50 hours or more, 60 hours or more, 70 hours or more, 80 hours or more, 90 hours or more, 100 hours or more, 120 hours or more, 130 h or more. In another aspect, the hydrolysis reaction time is 40-130 hours, 50-120 hours, 60-120 hours, 60-110 hours, 60-100 hours, 70-100 hours, 70-90 hours or 70-80 hours. Due to the stability of the enzyme composition longer hydrolysis reaction times are possible with corresponding higher sugar yields.

The pH during hydrolysis may be chosen by the skilled person. In a further aspect of the invention, the pH during the hydrolysis may be 3.0-6.4. The stable enzymes of the invention may have a broad pH range of up to 2 pH units, up to 3 pH units, up to 5 pH units. The optimum pH may lie within the limits of pH 2.0 to 8.0, 3.0-8.0, 3.5-7.0, 3.5-6.0 3.5-5.0, 3.5-4.5, 4.0-4,5 or is about 4.2.

In a further aspect of the invention the hydrolysis step c) is conducted until 70% or more, 80% or more, 85% or more, 90% or more, 92% or more, 95% or more of available sugar in lignocellulosic material is released.

Significantly, a process of the invention may be carried out using high levels of dry matter (of the lignocellulosic material) in the hydrolysis reaction. Thus, the invention may be carried out with a dry matter content of about 5% or higher, about 8% or higher, about 10% or higher, about 11% or higher, about 12% or higher, about 13% or higher, about 14% or higher, about 15% or higher, about 20% or higher, about 25% or higher, about 30% or higher, about 35% or higher or about 40% or higher. In a further embodiment, the dry matter content in the hydrolysis step c) is 14%, 15%, 16%, 17%, 18%, 19%, 20%, 21%, 22%, 23%, 24%, 25%, 26%, 27%, 28%, 29%, 30%, 31%, 32%, 33% (w/dmw) or more or 14-33%. The abbreviation dmw herein means "dry matter weight", weights are expressed in g (gram).

Fermentation

The process according to the invention comprises a fermentation step d). In a further aspect, the invention thus includes in step d) fermentation processes in which a microorganism is used for the fermentation of a carbon source comprising sugar(s), e.g. glucose, L-arabinose and/or xylose. The carbon source may include any carbohydrate oligo- or polymer comprising L-arabinose, xylose or glucose units, such as e.g. lignocellulose, xylans, cellulose, starch, arabinan and the like. For release of xylose or glucose units from such carbohydrates, appropriate carbohydrases (such as xylanases, glucanases, amylases and the like) may be added to the fermentation medium or may be produced by the modified host cell. In the latter case the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose. In a preferred process the modified host cell ferments both the L-arabinose (optionally xylose) and glucose, preferably simultaneously in which case preferably a modified host cell is used which is insensitive to glucose repression to prevent diauxic growth. In addition to a source of L-arabinose, optionally xylose (and glucose) as carbon source, the fermentation medium will further comprise the appropriate ingredient required for growth of the modified host cell. Compositions of fermentation media for growth of microorganisms such as yeasts or filamentous fungi are well known in the art.

The fermentation time may be shorter than in conventional fermentation at the same conditions, wherein part of the enzymatic hydrolysis still has to take part during fermentation. In one embodiment, the fermentation time is 100 hours or less, 90 hours or less, 80 hours or less, 70 hours or less, or 60 hours or less, for a sugar composition of 50 g/l glucose and corresponding other sugars from the lignocellulosic feedstock (e.g. 50 g/l xylose, 35 g/l L-arabinose and 10 g/l galactose. For more dilute sugar compositions the fermentation time may correspondingly be reduced.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$. Thus, in a preferred anaerobic fermentation process pyruvate is used as an electron (and hydrogen acceptor) and is reduced to fermentation products such as ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotics and a cephalosporin. In a preferred embodiment, the fermentation process is anaerobic. An anaerobic process is advantageous since it is cheaper than aerobic processes: less special equipment is needed. Furthermore, anaerobic processes are expected to give a higher product yield than aerobic processes. Under aerobic conditions, usually the biomass yield is higher than under anaerobic conditions. As a consequence, usually under aerobic conditions, the expected product yield is lower than under anaerobic conditions.

In another embodiment, the fermentation process is under oxygen-limited conditions. More preferably, the fermentation process is aerobic and under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used. Preferably, in a process under oxygen-limited conditions, the rate of oxygen consumption is at least 5.5, more preferably at least 6 and even more preferably at least 7 mmol/L/h.

The fermentation process is preferably run at a temperature that is optimal for the modified cell. Thus, for most yeasts or fungal cells, the fermentation process is performed at a temperature which is less than 42° C., preferably less than 38° C. For yeast or filamentous fungal host cells, the fermentation process is preferably performed at a temperature which is lower than 35, 33, 30 or 28° C. and at a temperature which is higher than 20, 22, or 25° C.

In an embodiment of the invention, in step d) the fermentation is conducted with a microorganism that is able to ferment at least one C5 sugar. In an embodiment the process is a process for the production of ethanol whereby the process comprises the step d) comprises fermenting a medium containing sugar(s) with a microorganism that is able to ferment at least one C5 sugar, whereby the host cell is able to ferment glucose, L-arabinose and xylose to ethanol. In an embodiment thereof the microorganism that is able to ferment at least one C5 sugar is a yeast. In an embodiment, the yeast is belongs to the genus *Saccharomyces*, preferably of the species *Saccharomyces cerevisiae*, in which the following genetic modifications have been made:
  a) a cluster consisting of PPP-genes TAL1, TKL1, RPE1 and RKI1, under control of strong promoters,
  b) a cluster consisting of a xylA-gene and the XKS1-gene both under control of constitutive promoters,
  c) a duster consisting of the genes araA, araB and araD and/or a duster of xylA-gene and the XKS1-gene;
  d) deletion of an aldose reductase gene;
    and adaptive evolution of the resulting modified microorganism. Such a microorganism and its preparation is described in more detail in WO 2008/041840 and in European Patent Application EP10160622.6, filed 21 Apr. 2010. In an embodiment, the fermentation process for the production of ethanol is anaerobic. Anaerobic has already been defined earlier herein. In another preferred embodiment, the fermentation process for the production of ethanol is aerobic. In another preferred embodiment, the fermentation process for the production of ethanol is under oxygen-limited conditions, more preferably aerobic and under oxygen-limited conditions. Oxygen-limited conditions have already been defined earlier herein.

In such process, the volumetric ethanol productivity is preferably at least 0.5, 1.0, 1.5, 2.0, 2.5, 3.0, 5.0 or 10.0 g ethanol per litre per hour. The ethanol yield on L-arabinose and optionally xylose and/or glucose in the process preferably is at least 20, 25, 30, 35, 40, 45, 50, 60, 70, 80, 90, 95 or 98%. The ethanol yield is herein defined as a percentage of the theoretical maximum yield, which, for glucose and L-arabinose and optionally xylose is 0.51 g. ethanol per g. glucose or xylose.

In one aspect, the fermentation process leading to the production of ethanol, has several advantages by comparison to known ethanol fermentations processes:
  anaerobic processes are possible;
  oxygen limited conditions are also possible;
  higher ethanol yields and ethanol production rates can be obtained;
  the strain used may be able to use L-arabinose and optionally xylose.

Alternatively to the fermentation processes described above, at least two distinct cells may be used, this means this process is a co-fermentation process. All preferred embodiments of the fermentation processes as described above are also preferred embodiments of this co-fermentation processe: identity of the fermentation product, identity of source of L-arabinose and source of xylose, conditions of fermentation (aerobical or anaerobical conditions, oxygen-limited conditions, temperature at which the process is being carried out, productivity of ethanol, yield of ethanol).

The fermentation process may be carried out without any requirement to adjust the pH during the process. That is to say, the process is one which may be carried out without the addition of any acid(s) or base(s). However, this excludes a pretreatment step, where acid may be added. The point is that the composition of the invention is capable of acting at low pH and, therefore, there is no need to adjust the pH of acid of an acid pretreated feedstock in order that saccharification may take place. Accordingly, a method of the invention may be a zero waste method using only organic products with no requirement for inorganic chemical input.

Overall Reaction Time

According to the invention, the overall reaction time (i.e the reaction time of hydrolysis step c) and fermentation step d) together may be reduced. In one embodiment, the overall reaction time is 150 hours or less, 140 hours or less, 130 or less, 120 hours or less, 110 hours or less, 100 hours of less, 90 hours or less, 80 hours or less, 75 hours or less, or about 72 hours at 90% glucose yield. Correspondingly lower overall times may be reached at lower glucose yield. This is independent on the mode in which the processes are conducted in SHF or SSF mode.

Fermentation Products

Fermentation products which may be produced according to the invention include amino acids, vitamins, pharmaceuticals, animal feed supplements, specialty chemicals, chemical feedstocks, plastics, solvents, fuels, or other organic polymers, lactic acid, and ethanol, including fuel ethanol (the term "ethanol" being understood to include ethyl alcohol or mixtures of ethyl alcohol and water).

Specific value-added products that may be produced by the methods of the invention include, but not limited to, biofuels (including ethanol and butanol); lactic acid; 3-hydroxy-propionic acid; acrylic acid; acetic acid; 1,3-propanediol; ethylene; glycerol; a plastic; a specialty chemical; an organic acid, including citric acid, succinic acid and maleic acid; a solvent; an animal feed supplement; a pharmaceutical such as a β-lactam antibiotic or a cephalosporin; a vitamin; an amino acid, such as lysine, methionine, tryptophan, threonine, and aspartic acid; an enzyme, such as a protease, a cellulase, an amylase, a glucanase, a lactase, a lipase, a lyase, an oxidoreductase, a transferase or a xylanase; a chemical feedstock; or an animal feed supplement.

Separation of Fermentation Product

The process according to the invention optionally comprises recovery of fermentation product. A fermentation product may be separated from the fermentation broth in any known manner. For each fermentation product the skilled person will thus be able to select a proper separation technique. For instance ethanol may be separated from a yeast fermentation broth by distillation, for instance steam distillation/vacuum distillation in conventional way.

Certain embodiments of the invention will below be described in more detail, but are in no way limiting the scope of the present invention.

Use of Thermostable Enzymes Under Optimal Temperature Conditions

In one embodiment, the invention relates to the use of thermostable enzymes such as cellulolytic enzymes of *Talaromyces* in Separate Hydrolysis and Fermentation (SHF) and SSF processes for the production of reducing sugars from pre-treated ligno-cellulosic feedstock in, but not limiting to, ethanol production. Cellulolytic enzymes of *Talaromyces* applied on pre-treated ligno-cellulosic feedstock showed maximal conversion rates at temperature within the range of 50-70° C. The enzyme remains active under these circumstances for 14 days and more without complete cessation of activity.

By using optimal temperature conditions, maximal amount of reducing sugars can be released from feedstock (total hydrolysis) within the shortest possible hydrolysis time. In this way, 100% conversion of cellulose in glucose is achieved in less than 5 days (120 h, see FIG. 1) in an SHF process with an enzyme dosage of 0.175 mL (6 mg protein)/g feedstock dry matter. Under SSF conditions at 33° C. the total conversion of the cellulose in ligno-cellulosic feedstock will last approx. 168 h [2] and herewith these mesophilic conditions determine the process time required for maximal ethanol production from feedstock.

In case thermo stable cellulolytic enzymes, such as from *Talaromyces*, are used in an SSF process with thermophilic ethanol-producing microorganisms, fermentation times will be shorter as cellulolytic enzymes of *Talaromyces* release the reducing sugars faster at higher temperatures than at mesophilic temperatures.

In SSF operation, the product concentration (g/L) is dependent on the amount of glucose produced, but this is not visible since sugars are converted to product in the SSF, and product concentrations can be related to underlying glucose concentration by multiplication with the theoretical maximum yield (Yps max in gr product per gram glucose)

The theoretical maximum yield (Yps max in gr product per gram glucose) of a fermentation product can be derived from textbook biochemistry. For ethanol, 1 mole of glucose (180 gr) yields according to normal glycolysis fermentation pathway in yeast 2 moles of ethanol (=2×46=92 gr ethanol. The theoretical maximum yield of ethanol on glucose is therefore 92/180=0.511 gr ethanol/gr glucose.

For Butanol (MW 74 gr/mole) or iso butanol, the theoretical maximum yield is 1 mole of butanol per mole of glucose. So Yps max for (iso-)butanol=74/180=0.411 gr (iso-)butanol/gr glucose.

For lactic acid the fermentation yield for homolactic fermentation is 2 moles of lactic acid (MW=90 gr/mole) per mole of glucose. According to this stoichiometry, the Yps max=1 gr lactic acid/gr glucose.

For other fermentation products a similar calculation may be made.

The cost reduction achieved with applying cellulolytic enzymes of *Talaromyces* will be the result of an overall process time reduction.

Process-Time Reduction with Thermostable Enzymes

Since stable enzymes allow extended hydrolysis time without significant losses in activity, hydrolysis times of e.g. 72 hours can be applied, resulting in conversions of approximately 90% of the theoretical maximum of reducing sugars obtained with only 0.175 mL enzyme/g feedstock dry-matter (see FIG. 1, point A). The mash so obtained can be used as substrate in a successive fermentation step for, for instance but not limiting to, ethanol production. The remaining approximately 10% of the cellulose, which is not yet converted into reducing sugars, will be converted into reducing sugars and directly into ethanol during the fermentation (SSF). Since such fermentation starts with 90% of the maximal amount of sugars available at the beginning of the fermentation, the release rate of reducing sugars will not determine the growth rate of the ethanol-producing microorganism as it does during conventional SSF. In this way, the ethanol production can take place at higher production rates, allowing completion of ethanol production in less than 48 h, less than 45 h, less than 40 h, less than 35 h, less than 30 h, less than 25 h, e.g. 24 h. The overall process time can thus be reduced from 7 days to less than 5 days, to less than 4 days, to less than 3 days, to less than 2 days (48 hours) Due to the shorter fermentation times, less substrate is used for maintenance of the ethanol producing microorganism. The overall yield of this approach of extending the hydrolysis time and shortening the fermentation time may result in 5-15% higher ethanol on substrate yields in comparison with conventional pre-saccharification and SSF.

The cost reduction achieved with applying stable cellulolytic enzymes, like those of *Talaromyces*, in this way will result from the overall process time reduction.

Figure 2:
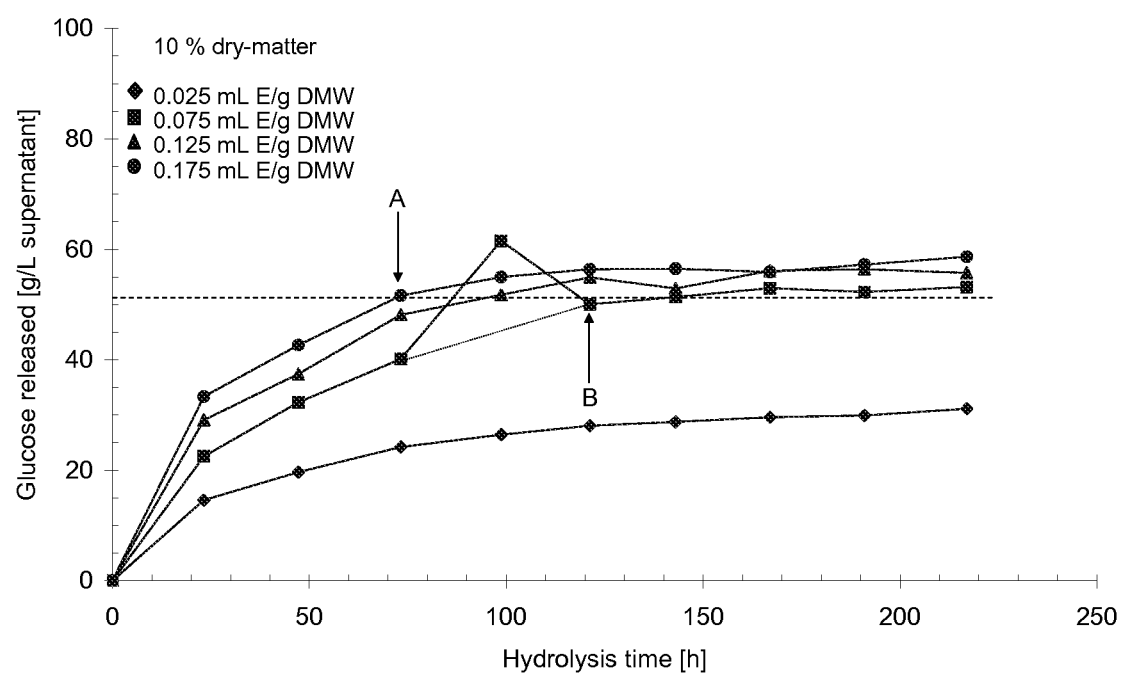
FIG. 2: Release of the reducing sugar glucose during hydrolysis of pre-treated ligno-cellulosic feedstock at different *Talaromyces* enzyme dosages (expressed as volume enzyme solution per amount of feedstock dry-matter). The dotted line indicates the 90% of the maximum theoretical amount of glucose that can be produced from the feedstock (90% conversion). A indicates the moment 90% hydrolysis is achieved with a 0.175 mL enzyme solution/g feedstock dry matter dosage; B indicates the moment 90% conversion is achieved with a 0.075 mL enzyme solution/g feedstock dry matter dosage.

Compensation of Lower Enzyme Dosage with Extended Hydrolysis Time Using *Talaromyces* Enzymes Due to the high stability of the stable enzymes, the activities do not cease in time, although less reducing sugars are liberated in the course of the hydrolysis. It is possible to lower the enzyme dosage and extend the use of the enzyme by prolonging the hydrolysis times to obtain similar levels of released reducing sugars. For example, 0.175 mL enzyme/g feedstock dry-matter resulted in release of approximately 90% of the theoretical maximum of reducing sugars from pre-treated feedstock within 72 h (point A in FIG. 2). When using 0.075 mL enzyme/g feedstock dry-matter, approximately 90% conversion of the theoretical maximum is achieved within 120 h (point B in FIG. 2). The results show that, because of the stability of the enzyme activity, lowering the enzyme dosage can be compensated by extending the hydrolysis time to obtain the same amount of reducing sugars. The same holds for hydrolysis of pre-treated feedstock at dry-matter contents higher than 10% shows that compensating effect of extended hydrolysis time at 15% dry matter feedstock.

The cost reduction achieved by using stable cellulolytic enzymes, such as of *Talaromyces*, results from requiring less enzyme dosage, resulting in similar hydrolysis conversion yields.

Fermentation Process Optimization with Stable Enzymes

If hydrolysis results in reducing sugar levels at or close to the theoretical maximum of reducing sugars from pre-treated feedstock, the reducing sugars solution can be adjusted and processed with the aim to obtain optimal substrate solution composition for the fermentation step. This adjustment and processing includes, but not limits to, concentration, purification, pH adjustment, supplementation of additional nutrients, etc. the fermentation can be started by transferring the reducing sugars solution to the fermentation vessel, or by adding the necessary nutrient and inoculum to the vessel containing the reducing sugars solution.

In addition, the mode of adding the reducing sugars solution to the fermentation vessel, can be optimized for maximal fermentation efficiency, such as addition under carbon limiting conditions, in batch, fed-batch and continuous mode.

Due to the stability of the enzymes, activity will remain present during the fermentation and will continue to convert the remaining cellulose and partly hydrolysed cellulose into reducing sugars. In this way, stable enzymes allow optimization of the fermentation step without losses in overall conversion yields.

The cost reduction achieved with applying stable cellulolytic enzymes, such as of of *Talaromyces*, in this way will result from maximizing the process efficiency.

Lowering the Risk on Contamination with Stable Enzymes

In a common process for converting ligno-cellulosic material into ethanol, process steps are preferably done under septic conditions to lower the operational costs. Contamination and growth of contaminating microorganisms can therefore occur and result in undesirable side effects, such lactic acid, formic acid and acetic acid production, yield losses of ethanol on substrate, production of toxins and extracellular polysaccharides, which may affect production costs significantly. A high process temperature and/or a short process time will limit the risk on contamination during hydrolysis and fermentation. Thermo stable enzymes, like those of *Talaromyces*, are capable of hydrolysing ligno-cellulosic feedstock at temperatures of higher than 60° C. At these temperatures, the risk that a contaminating microorganism will cause undesired side effects will be little to almost zero.

During the fermentation step, in which ethanol is produced, temperatures are typically between 30-37° C. and will preferably not be raised because of production losses. By applying fermentation process times as short as possible the risks and effects of contamination and/or growth of contaminants will be reduced as much as possible. With stable enzymes, like those of *Talaromyces*, a short as possible fermentation times can be applied (see description above), and thus risks on contamination and/or growth of contaminants will be reduced as much as possible. The cost reduction achieved with applying thermo stable cellulolytic enzymes of *Talaromyces* in this way will result from lower risk of process failures due to contamination.

Stable Enzymes Reduce Cooling Costs and Increase Productivity of Ethanol Plants

The first step after thermal pretreatment will be to cool the pretreated feedstock to temperatures where the enzymes are optimal active. On large scale, this is typically done by adding (cooled) water, which will, besides decreasing the temperature, reduce the dry-matter content. By using thermos stable enzymes, like those of *Talaromyces*, cost reduction can be achieved by the fact that (i) less cooling of the pretreated feedstock is required since higher temperatures are allowed during hydrolysis, and (ii) less water will be added, which will increase the dry-matter content during hydrolysis and fermentation and thus increase the ethanol production capacity (amount produced per time unit per volume) of an ethanol plant. Also, by using thermostable enzymes according to the invention, like those of *Talaromyces*, cost reduction may also be achieved by using cooling water having higher temperature that the water that is used in a process with non-thermostable enzyme.

Enzyme Recycling after Hydrolysis with Stable Enzymes

Figure 3:
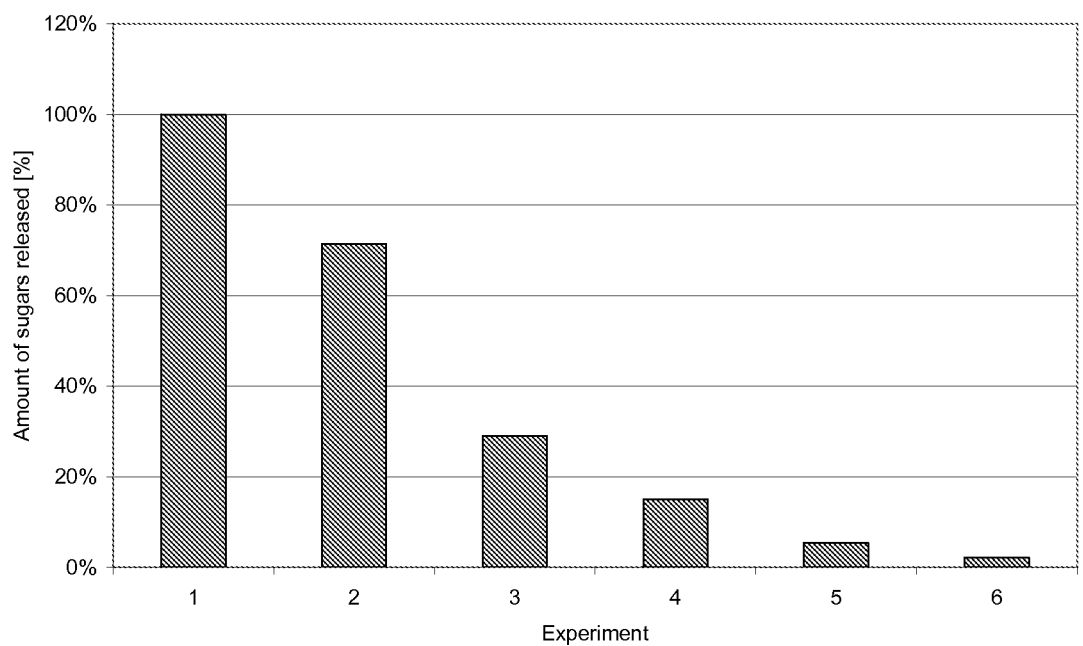
FIG. 3: Amount of sugars that is released during 72 hours 60° C. hydrolysis of feedstock if recycled *Talaromyces* enzymes are used. The graph shows 5 cycles of enzyme recycling (experiment 2-6). In each cycle the amount of enzyme recovered from the previous cycle is used to hydrolyse a new batch of pretreated feedstock. No new enzymes are added. Recovery is done by using centrifugation and ultra filtration. The amount of sugars released per cycle is compared to the amount released in experiment 1 where *Talaromyces* enzymes are used which are not recycled.

At the end of the hydrolysis, enzyme activities appear to be low since little reducing sugars are released once almost all cellulose is converted. The amount of enzymatic activity present, however, has decreased only a little, assumingly mainly due to absorption of the enzymes to the substrate. By applying solid-liquid separation after hydrolysis, such as centrifugation, filtration, sedicantation, etcetera, 60% or more e.g. 70% of the enzyme activity in solution can be recovered and re-used for hydrolysis of a new pre-treated ligno-cellulosic feedstock during the next hydrolysis (See FIG. 3).

More over, after solid-liquid separation the enzyme in solution can be separated from the solution containing reducing sugars and other hydrolysis products from the enzymatic actions. This separation can be done by, but not limiting to, (ultra and micro)filtration, centrifugation, sedicantation, sedimentation, with or without first adsorption of the enzyme to a carrier of any kind.

For example, after hydrolysis of pre-treated feedstock with 0.175 mL/g feedstock dry matter enzyme load for 20 h, 50% of the theoretical maximum amount of reducing sugars is liberated and after the same hydrolysis for 72 h, 90% of the theoretical maximum amount of reducing sugars is liberated. By centrifugation and ultrafiltration, 60-70% of the enzyme activity was recovered in the retentate, while the filtrate contained more than 80% of the liberated reducing sugars. By re-using the retentate, either as it is or after further purification and/or concentration, enzyme dosage during the next hydrolysis step can be reduced with 60-70%. The cost reduction achieved by using stable cellulolytic enzymes, such as of *Talaromyces*, in this way results from requiring less enzyme dosage.

Enzyme Recycling after Hydrolysis i.c.w. Enzyme Production and Yeast-Cell Recycling with Stable Enzymes The process including enzyme recycling after hydrolysis, as described above, can be combined with recycling of the ethanol producing microorganism after fermentation and with the use of the reducing sugars containing filtrate as a substrate (purified and/or concentrated or diluted) in enzyme-production fermentation and as substrate for the cultivation of the ethanol-producing microorganism.

Enzyme Recycling after Vacuum Distillation with Stable Enzymes

Figure 5:
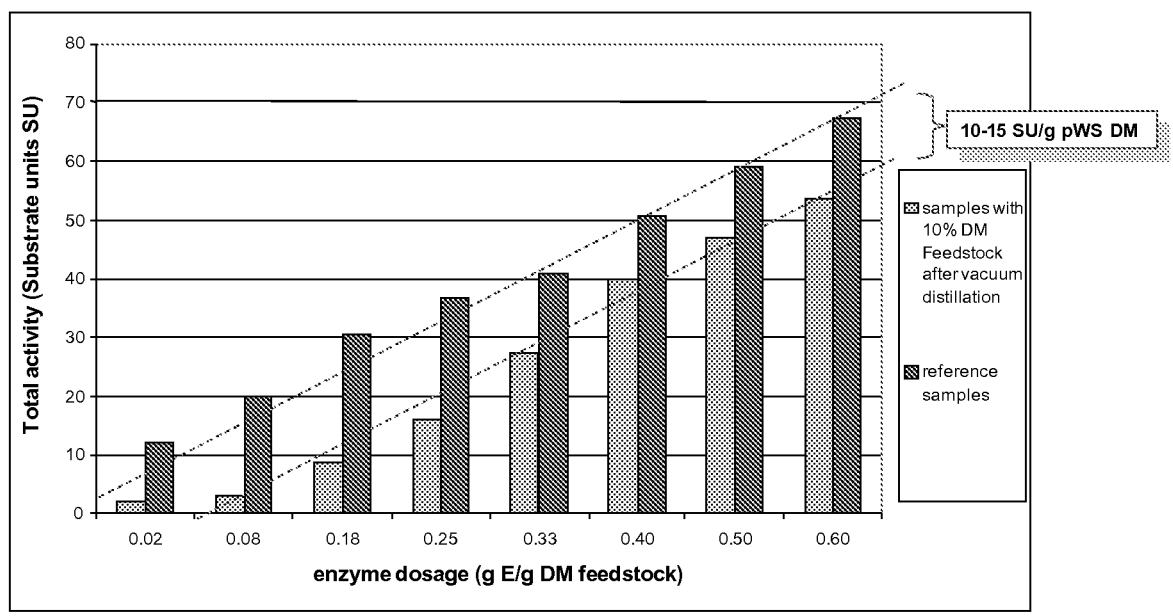
FIG. 5: The total amount of enzyme activity, expressed per Substrate units, before (reference samples) and after hydrolysis, fermentation and vacuum distillation of a 10% dry-matter feedstock suspension at several enzyme dosages. One substrate unit enzyme activity releases one mmol reducing sugar.

The thermo stability of enzymes, like those from *Talaromyces*, causes remaining cellulolytic activity after hydrolysis, fermentation and vacuum distillation in the thin stillage. The total activity of the enzyme is reduced during the three successive process steps with 10-15 Substrate units per g dry-matter feedstock, independently of the initial enzyme dosage (see FIG. 5). The thin stillage obtained after vacuum distillation can thus be re-used as a source of enzyme for a newly started hydrolysis-fermentation-distillation process cycle of pre-treated wheat straw conversion into ethanol. The thin stillage can be used either in concentrated or (un)diluted form and/or purified and with or without additional enzyme supplementation.

Re-use of thin stillage for hydrolysis of cellulosic material, corn grids and lactose is described for a multi-stage SSF reactor [2], aiming at continuous production and separation of volatile fermentation products. In this system, a gas-liquid contacting column is used to continuous separate the ethanol from the mash. The complex system, however, requires enormous amounts of enzymes to achieve fast-enough release of reducing sugars from the ligno-cellulosic feedstock since as process conditions are sub-optimal for the enzyme used. The cost reduction achieved by using thermo stable cellulolytic enzymes, like those of *Talaromyces*, in this way results from the ability to re-use the enzyme activity.

Enzyme Recycling in Combination with Enzyme Supplementation after Vacuum Distillation with Thermo Stable Enzymes In an optimal process, an amount of enzyme is supplemented into the thin stillage, before its re-use in a new process cycle, equal to the amount of activity lost during the three successive process steps of the previous process cycle. In this way over-dosage of enzyme is avoided and thus most efficient use of enzyme is obtained.

More over, by providing high enzyme dosage in the first process cycle, and supplementing enzyme equal to the amount of activity lost during the three successive process steps in the following process cycles, highest possible hydrolysis rates can be obtained in each process cycle resulting in short hydrolysis times of less than 48 h in combination with most efficient use of enzymes.

Use of Stable Enzymes in Mixed Systems

By applying mixing during hydrolysis, enzymes come more often in contact with substrates, which results in a more efficient use of the catalytic activity. This will result in a lower enzyme dosages and thus in lower costs, unless the mixing has a negative effect on the enzymes. Stable enzymes, like the thermo stable enzymes from *Talaromyces*, are robust and can resist circumstances of (locally) high shear and temperatures, which is the case during intensive mixing of slurries. The use of it in mixed systems is therefore beneficial and will lead to dosage and thus costs reduction.

The invention is further described by the following examples, which should not be construed as limiting the scope of the invention.

EXAMPLES

Example 1

Reduction of Process Time by Using Enzyme Composition that Retains Activity for More than 30 Hours at Elevated Temperatures

A comparison is made between a process in which hydrolysis is extended to 72 hours and a process in which the time for hydrolysis is limited to 20 hours to demonstrate the benefit of using the retained activity of the enzyme composition in an extended hydrolysis.

Materials and Methods

The method of hydrolysis and fermentation is described in patent application WO2010018105 (PCT/EP2009/060098). Pre-treated wheat straw was used as feedstock and washed in tap water of 70 degrees C. until pH was higher than 3, preferably between 6.0 and 6.5. A slurry of 10% w/w of the washed pre-treated feedstock was prepared and pre-incubated at 56 degree C. Enzyme composition was added at a concentration of 0.20 g enzyme composition per g feedstock dry matter. The mixture was divided in two equal portions A and B and incubated at 56 degree C. in an incubator while smoothly shaken. During this hydrolysis, samples were taken daily to determine the amount of glucose released from the cellulose present in the slurry. Portion A represents the process in which a hydrolysis time of 20 hours is used; portion B represents the process in which the retained activity is used in an extended hydrolysis of 72 hours.

After 20 hours, portion A was taken from the incubator and cooled to 33 degree C. Fermentation was performed, according to WO2010018105 (PCT/EP2009/060098), by the addition of yeasts cells and salts and incubating at 33 degrees C. for an additional 6 days. The process time of portion A herewith amounts approximately 7 days (20 hours hydrolysis and 6 days fermentation).

After 72 hours, portion B was taken from the incubator and cooled to 33 degree C. Fermentation was performed at 33 degree C. in the same way as portion A but stopped after 48 hours. The process time of portion B herewith amounts 5 days (3 days hydrolysis and 2 days fermentation).

Results and Discussion

During fermentation, the released sugars are converted into yeast cells, $CO_2$ and ethanol. Once production of yeast cells is stopped, the amount of ethanol produced is proportional to the amount of carbon dioxide produced. Since carbon dioxide can be measured online, its production reflexes the amount of ethanol produced. Table 1 gives the amount of glucose released, the amount of carbon dioxide produced and the final yield of ethanol in portions A and B.

TABLE 1

Results of glucose, carbon dioxide and ethanol analysis of portion A and B.

| Process time [h] | Glucose [g/L] | | Carbon dioxide production [% of maximum] | | Ethanol [% v/v] | |
| --- | --- | --- | --- | --- | --- | --- |
| | Portion A | Portion B | Portion A | Portion B | Portion A | Portion B |
| 0 | 0 | 0 | 0 | 0 | | |
| 20 | 33 | 33 | 0 | 0 | | |
| 47 | 0 | 43 | 80 | 0 | | |
| 72 | 0 | 52 | 91 | 0 | | |
| 120 | 0 | 0 | 98 | 100 | | 2.1 |
| 168 | 0 | — | 100 | — | 2.1 | — |

The results show that a hydrolysis period of 20 hours, followed by a fermentation period of 6 days yield the same amount of ethanol as a hydrolysis period of 72 hours followed by a fermentation of 48 hours. Thus with a process time of 5 days, a similar ethanol production level is achieved as with a process time of 7 days.

The reason for this is that during the 20 hours hydrolysis in portion A less than 60% of the theoretical maximal amount of sugars is released. The remaining amount is released during the fermentation, though under less optimal conditions due to the lower temperature.

In portion B the enzyme composition retained activity during the hydrolysis period of 72 hours at more optimal conditions. During this hydrolysis, 95% of the theoretical maximum amount of glucose is released, while the remaining amount of 5% is released during the 48 hours fermentation period. Herewith it is demonstrated that the retaining activity of the enzyme composition can be used to shorten the process time and thus lower the operational costs.

Example 2

Reduction of Enzyme Dosage by Increasing the Process Time with Enzyme Composition that Retain Active for More than 30 Hours at Elevated Temperatures

In another experiment, the property of retaining activity of the enzyme composition was used to compensate low enzyme dosage by extended hydrolysis.

Materials and Methods

The method of hydrolysis and fermentation as referred to in Example 1 was used.

A slurry of 10% w/w of the washed pre-treated feedstock was prepared and pre-incubated at 56 degree C. The slurry was divided in to two equal portions A and B. Enzyme composition was added at a concentration of 0.20 g enzyme composition per g feedstock dry matter to portion A and at a concentration of 0.09 g enzyme composition per g feedstock dry matter to portion B. The portions A and B were incubated at 56 degree C. in a incubator while smoothly shaken for 220 hours. During this hydrolysis, samples were taken daily to determine the amount of glucose released from the cellulose present in the slurry. The glucose measured is plotted against hydrolysis time (see FIG. 5).

In a separate experiment portions A, with 0.20 g enzyme composition per g feedstock dry matter, and portion B, with 0.09 g enzyme composition per g feedstock dry matter, were incubated at 56 degree C. After 72 hours (portion A) and 120 hours (portion B) the portions were taken from the incubator and cooled to 33 degree C. Fermentation was performed, according to WO2010018105 (PCT/EP20091/060098), by the addition of yeasts cells and salts and incubating at 33 degrees C. for an additional 48 hours.

Results and Discussion

Figure 6:
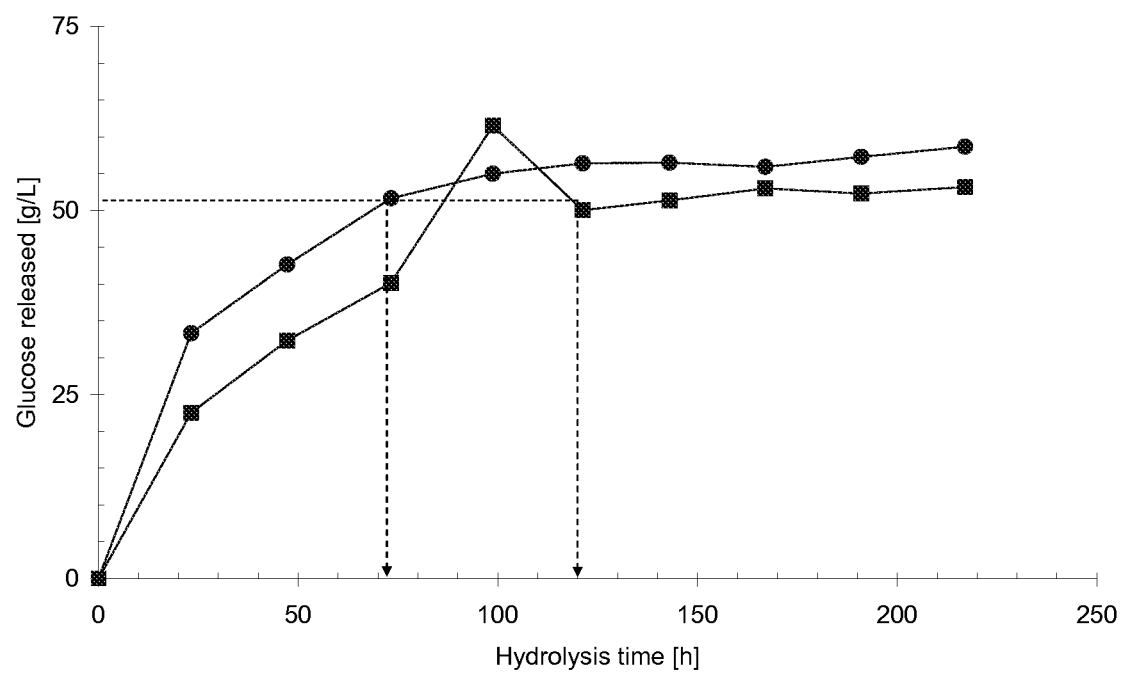
FIG. 6: Glucose release during hydrolysis with 0.20 (●) and 0.09 (■) g enzyme composition per g feedstock dry-matter (example 2).

FIG. 6 shows the release of glucose from cellulose in a 10% w/w dry-matter suspension of acid pre-treated feedstock at a dosage of 0.20 and 0.09 g enzyme composition per g feedstock dry-matter weight. It shows that while enzyme dosages are reduced, similar levels of glucose can be achieved if hydrolysis times are extended. Surprisingly, although the amount of enzyme is more than halved, an extension of 60% of the hydrolysis time was require to compensate for the lower enzyme dosage. The 52 g/L level is achieved within 72 hours when a dosage of 0.20 g enzyme composition per g feedstock dry-matter weight is used, while the same level is achieve in 120 hours when 0.09 g enzyme composition per g feedstock dry-matter weight is used.

In the separate experiment both portions were fermented after 72 (portion A) and 120 hours (portion B, see Table 2). Although hydrolysis time was 60% longer for portion B, similar ethanol levels were obtained after fermentation. In this way, it is demonstrated that the retaining activity of the enzyme composition can be used to lower the enzyme dosage, and thus to reduce the operational costs proportionally.

TABLE 2

Results of hydrolysis and fermentation, comparison of portions A and B.

| | Enzyme dosage [enzyme per g feedstock dmw] | Hydrolysis time [h] | Fermentation time [h] | Ethanol [% v/v] |
|---|---|---|---|---|
| Portion A | 0.20 | 72 | 48 | 2.0 |
| Portion B | 0.09 | 120 | 48 | 1.9 |

Example 3

Use of Enzyme Composition with Retaining Activity Allows Re-Use of Activity after Hydrolysis An experiment is performed to demonstrate the use of the liquid fraction of the feedstock-enzyme slurry after hydrolysis, as a source of activity for the hydrolysis in a next process cycle.

Materials and Methods

The method of hydrolysis as referred to in Example 1 is used.

A slurry of 10% w/w of the pre-treated feedstock is prepared and pre-incubated at 60 degree C. Enzyme composition is added at a concentration of 0.20 g enzyme composition per g feedstock dry matter and incubated at 56 degree C. in a incubator while smoothly shaken for 120 hours. The slurry is than taken from the incubator and centrifuged at 4500 g. the pellet is washed once, centrifuged and the washing supernatant is combined with the supernatant of the first solid-liquid separation. The combined supernatant is filtrated, using a Z200 filter (a about 0.2 um thick paperfilter by Pall) and concentrated using a spiral wound ultra-filtration unit of 10 kD PES at 10 degree C. The so obtained concentrate is used as enzyme source in a second hydrolysis with new pre-treated feedstock under the conditions as described above. All process streams are analyzed for glucose and enzyme activity.

Results and Discussion

Figure 4:
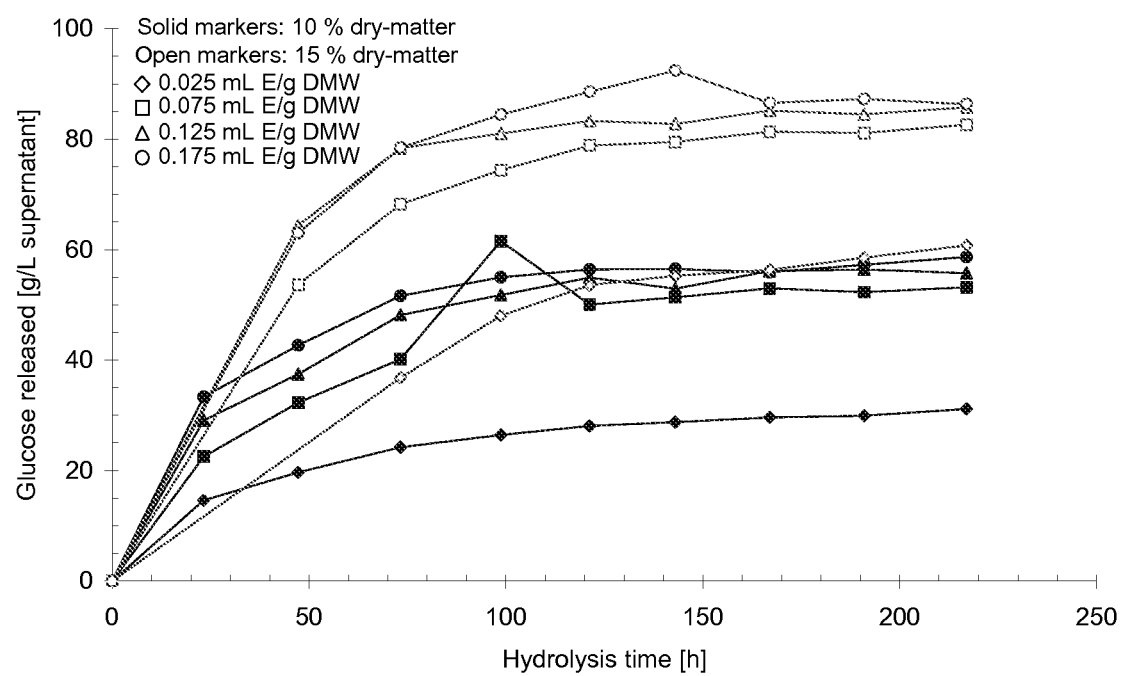
FIG. 4: Release of reducing sugar glucose during hydrolysis of pre-treated ligno-cellulosic feedstock at different *Talaromyces* enzyme dosages (expressed as volume enzyme solution per amount of feedstock dry-matter). Results of 10% w/w feedstock dry-matter and 15% w.w feedstock dry-matter are shown.

Analysis of the streams demonstrates that glucose can be separated from the enzyme by using solid-liquid separation, followed by filtration and ultra filtration. The enzyme activity of the UF concentrate remains at a level of 70% of the original activity after hydrolysis, as is shown in FIG. 4. This means that, using the enzyme composition with retaining activity and using the recovery steps described here, enzyme can be re-used for hydrolysis of feedstock in a successive process cycle. About 86% of the glucose is recovered, and can be used as a clean process stream in fermentation.

By recovery of enzyme activity after hydrolysis makes it possible to re-use this enzyme activity and thus to cut costs for enzymes. More over, the clean process stream containing the glucose will result in lower maintenance and energy costs as the result of absence of solids during fermentation and distillation.

Example 4

Use of Enzyme Composition with Retaining Activity Allows Re-Use of Activity after Distillation Example 4

Use of Enzyme Composition with Retaining Activity Allows Re-Use of Activity after Distillation An experiment is performed to demonstrate the use of thin-stillage, obtained after hydrolysis with enzyme composition with retaining activity, fermentation and distillation, as a source of activity for hydrolysis.

Materials and Methods

The method of hydrolysis and fermentation as referred to in Example 1 is used.

A slurry of 10% w/w of the washed pre-treated feedstock is prepared and pre-incubated at 56 degree C. Enzyme composition is added at a concentration of 0.20 g enzyme composition per g feedstock dry matter and incubated at 56 degree C. in a incubator while smoothly shaken for 20 hours. The slurry is than taken from the incubator and cooled to 33 degree C. Fermentation was performed, according to PCT/EP2009/060098, by the addition of yeasts cells and salts and incubating at 33 degrees C. for 148 hours.

The slurry is distilled, using vacuum distillation for 20 minutes at 100 mbar and 60±1 degree C. until all ethanol is removed. The slurry, containing insoluble residues, yeast cells and enzymes, is centrifuged to remove the insoluble residues and yeast cells; and the supernatant is collected. The supernatant is further on referred to as thin-stillage.

Pre-treated feedstock is added to the thin-stillage at a concentration of 10% dry-matter weight. The so obtained slurry is split in several equal portions to which each of them an amount of enzyme is added in the range of 0 to 0.58 g enzyme per g feedstock dry matter. The slurry is than incubated at 56 degree C. for 20 hours and the amount of glucose released.

Results and Discussion

To distinguish between high and low enzyme activities, hydrolysis should not last until all cellulose is hydrolyzed. Therefore, a hydrolysis time of 20 hours is used here. The amount of glucose released within these 20 hours depends on the amount of enzyme present during the hydrolysis. The maximum amount of glucose is the level indicated in FIG. 6, and is set to 100% here.

Figure 7:
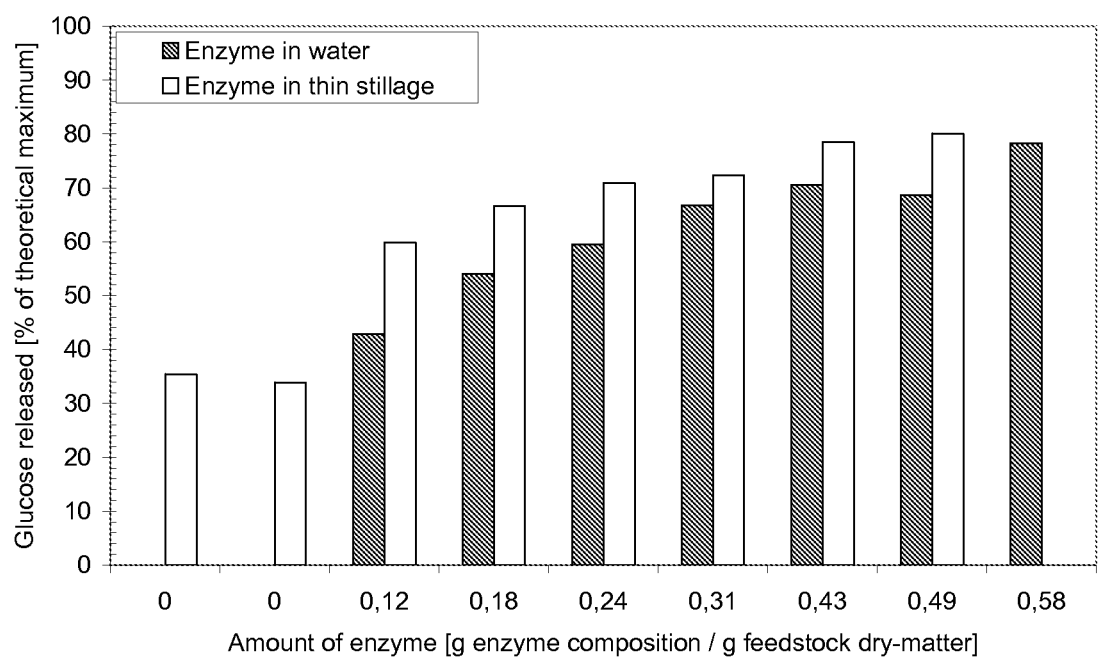
FIG. 7: The relative amount of glucose released from feedstock at different enzyme dosages in thin-stillage (example 4).
Figure 8:
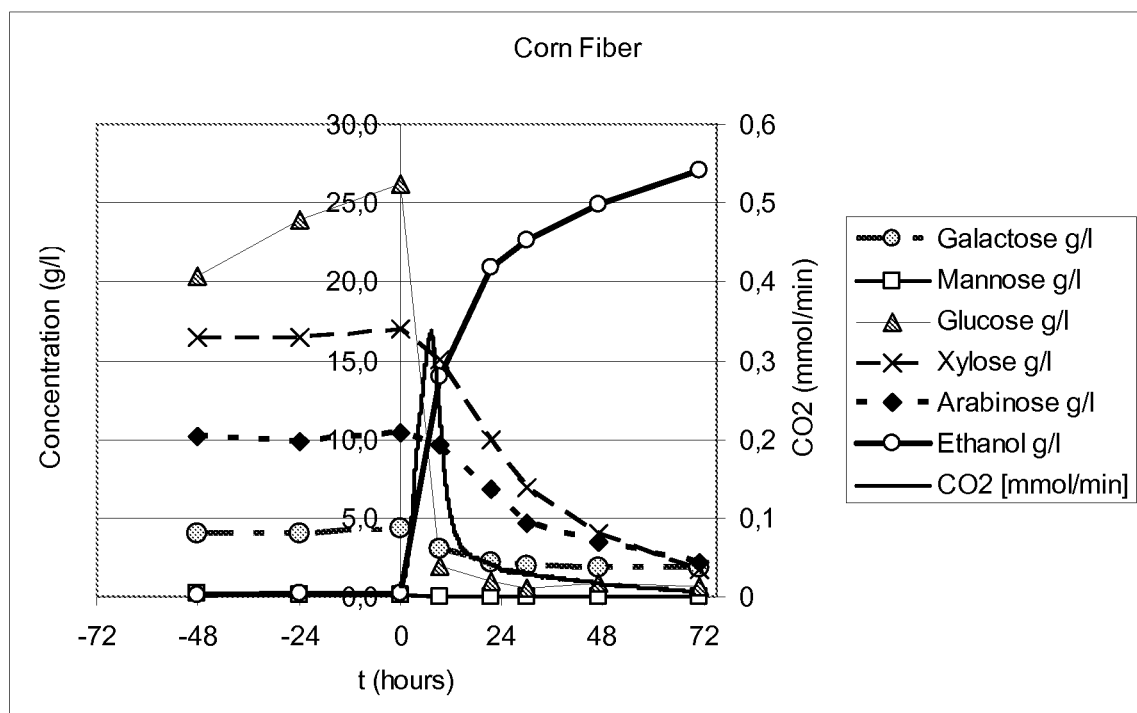
FIG. 8 sets out the performance of strain BIE252 in hydrolyzed corn fiber at 13.8% d.m. $CO_2$ production rate, ethanol production and sugar conversion are shown.
Figure 9:
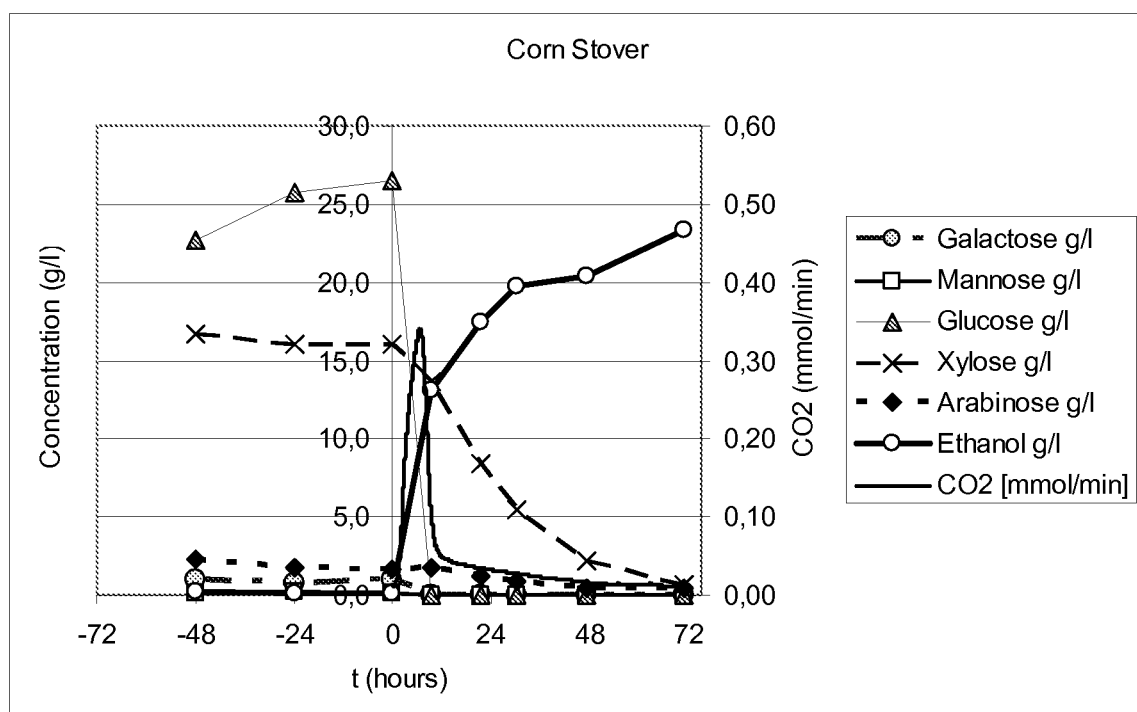
FIG. 9 sets out the performance of strain BIE252 in hydrolyzed corn stover at 10% d.m. $CO_2$ production rate, ethanol production and sugar conversion are shown.
Figure 10:
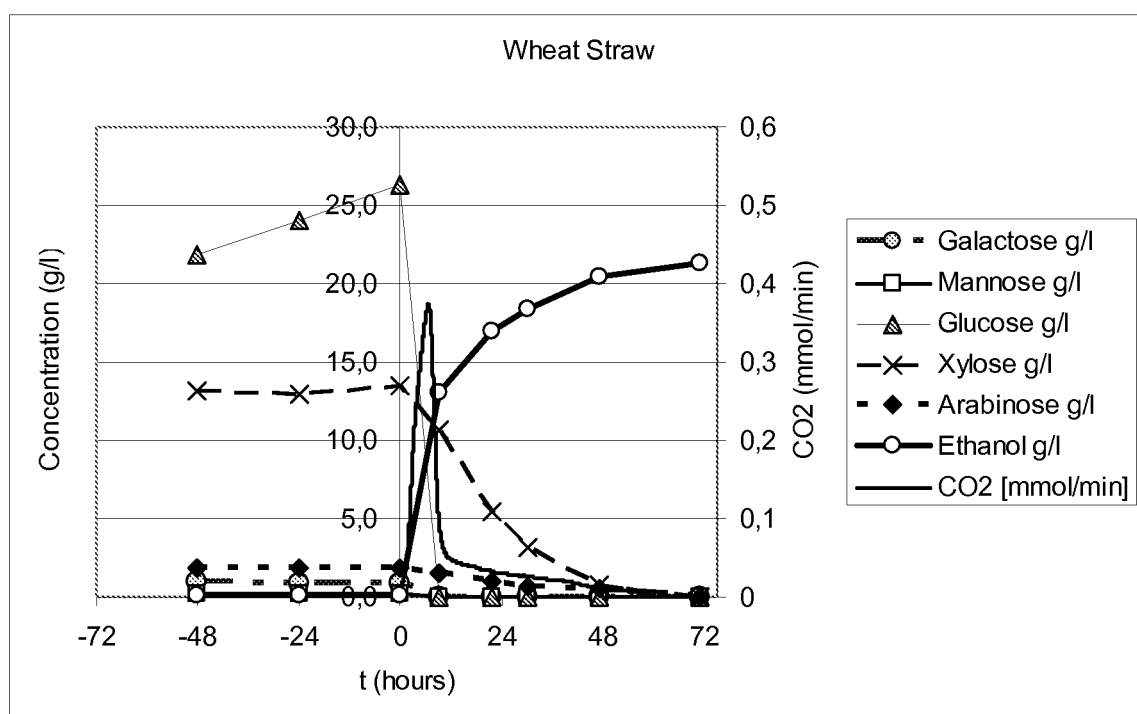
FIG. 10 sets out the performance of strain BIE252 in hydrolyzed wheat straw at 10% d.m. $CO_2$ production rate, ethanol production and sugar conversion are shown.

As can be seen in FIG. 7, thin-stillage without added enzyme contains hydrolytic activity that results from the use of enzyme composition with retaining activity in the earlier process cycle. Therefore, using enzyme composition suspended in thin-stillage enhances glucose release in comparison to enzyme composition suspended in water. This enhancement is more significant at lower enzyme dosages, which can be explained by the fact that with increasing enzyme activities, glucose release rates decrease earlier in time as is also shown in FIG. 7. The curve of the high enzyme dosage bend-off earlier than the curve of the low enzyme dosage.

By re-using thin-stillage in the hydrolysis, enzyme dosage can be reduced and thus cost reduction can be obtained.

Example 5

Enzymatic Hydrolysis of Lignocellulosic Material and Fermentation with C5 Converting Yeast Hydrolysis Dilute acid pretreated samples of corn stover and wheat straw were enzymatically hydrolyzed by using an experimental broad spectrum cellulase preparation at 60° C. for 3 days (72 hours). The pH at the start of the hydrolysis was 5.0. The dry matter content at the start of the hydrolysis was 10% w/w.

The conditions for the hydrolysis of pretreated corn fiber samples was essentially the same, except that the hydrolysis temperature was 50° C. and the dry matter content at the start of the hydrolysis was 13.8%.

After hydrolysis (72 hrs), the samples were allowed to be cooled to room temperature. The pH was adjusted to 5.5 using 10% NaOH. Subsequently, 1 milliliter of a 200 gram per liter (NH4)2SO4 and 1 milliliter of 100 gram per liter KH2PO4 was added.

Fermentation

Then, yeast samples were added corresponding to a yeast dry matter content of 1 gram yeast per kilogram hydrolysate. The CO2 evolution in time was followed using the AFM (Alcohol Fermentation Monitor; HaloteC Instruments BV, Veenendaal, the Netherlands). Experiments were performed in at least triplicate, for 72 hours at 33° C. One of these is sampled at regular intervals in order to be able to analyze ethanol formation and residual sugar concentrations. These data can be used to calculate fermentation yields. The broth of the other two experiments is not sampled. Instead, at the end of the fermentation the broth is distilled using a Buchi K-355 distillation unit at 45% steam for 15 minutes. The alcohol produced is being determined using an Anton Paar DMA 5000 density meter (Anton Paar Benelux BVBA, Dongen, the Netherlands).

The strain used for fermentation is BIE252, the preparation of which is described in European patent application EP10160622.6, filed 21 Apr. 2010. This strain is a *Saccharomyces cerevisiae* strain that has been genetically adapted to allow it to metabolize C5-sugars, i.e. xylose and arabinose.

BIE252 was cultured overnight in shake flasks containing YEP medium supplemented with 2% glucose. The cells were harvested by centrifugation at resuspended at a concentration of 50 grams dry matter per liter.

The feed stocks that were tested consisted of batches of corn fiber, corn stover and wheat straw. The hydrolysis and fermentation were performed as described in the materials and methods section.

The results are presented in FIGS. 17 (corn fiber), 18 (corn stover) and 19 (wheat straw). In case of corn stover and wheat straw, feedstocks with a relatively low amount of galactose and arabinose but mainly consisting of glucose and xylose, all sugars were converted in 72 hours into CO2 and ethanol. In case of corn fiber (FIG. 17), there is a low residual amount left of arabinose, galactose and xylose.

In the tables below the yield of the fermentation was calculated, on basis of the sugars liberated at the end of the hydrolysis and the amount of ethanol that was produced at the end of the fermentation.

TABLE 3

Total sugar released (g/l), ethanol produced (g/l) and ethanol yield (gethanol/gsugar) of fermentation of BIE252, for different lignocellulosic feedstock

| Lignocellulosic feedstock | Total sugar* (g/l) | Produced EtOH (g/l) | EtOH yield ($g_{ethanol}/g_{sugar}$) |
|---|---|---|---|
| Corn Stover | 45.4 | 22.7 | 0.50 |
| Wheat Straw | 42.7 | 20.7 | 0.48 |
| Corn Fiber | 58.1 | 27.4 | 0.47 |

*(released, monomeric sugar at start fermentation)

Based on the amount of ethanol produced at the end of the fermentation, as determined by the Anton Paar DMA 5000 density meter measurement, and the amount of pretreated feedstock that was being used, yields of the overall hydrolysis and fermentation were calculated, in duplicate. These figures are set out in table 4.

TABLE 4

Overall hydrolysis and fermentation yield (gallons of ethanol per ton dry matter) of fermentation of BIE252, for different lignocellulosic feedstock

| Lignocellulosic feedstock | Overall hydrolysis and fermentation yield (gallons of ethanol per ton dry matter) $1^{st}$ fermentation | Overall hydrolysis and fermentation yield (gallons of ethanol per ton dry matter) $2^{nd}$ fermentation |
|---|---|---|
| Corn Stover | 81 | 81 |
| Wheat Straw | 72 | 73 |
| Corn Fiber | 67 | 69 |

LITERATURE

[1] Badger, P, Ethanol from cellulose: a general review, Trends in new crops and new uses. 2002. J. Janick and A. Whipkey (eds.). ASHS Press, Alexandria, Va.;
[2] Kumar, S., Chem. Eng. Technol. 32 (2009) 517-526;
[3] WO 2007/091231
[4] Murray, P., et al., Enzyme Microbial Technol 29 (2001) 90-98;
[5] Dow, N., and McMillian, J. Technical Report NREL/TP-510-42630, January 2008;
[6] U.S. Pat. No. 5,141,861;
[7] WO 2008/008793.

The invention claimed is:

1. A process for preparing a biofuel from corn fiber, corn stover or wheat straw comprising:
   a) pre-treating the corn fiber, corn stover or wheat straw;
   b) enzymatically hydrolyzing the corn fiber, corn stover or wheat straw to produce a hydrolysate;
   c) fermenting the hydrolysate into a biofuel; and
   d) recovering the biofuel;

wherein enzymes used in step b) comprise of a broth resulting from growth of a filamentous fungal strain in a medium, which have a temperature optimum of 50-70° C.;

wherein a dry matter content of said corn fiber, corn stover or wheat straw in step b) is about 10-33% by weight;

wherein step b) is performed at a pH from about 4-6;

wherein step b) results in a release of at least 70% of available sugar in the corn fiber, corn stover or wheat straw;

wherein step b) occurs from 40-130 hours at a temperature of 50-70° C.; and wherein in step c), the fermentation is conducted with a yeast strain that is able to ferment at least one C5 sugar selected from the group consisting of arabinose and xylose.

2. The process of claim 1 which uses said corn stover.

3. The process of claim 1 which uses said wheat straw.

4. The process of claim 1 which uses said corn fiber.

5. The process of claim 1, wherein step b) is performed for about 72 to 120 hours.

6. The process of claim 1, wherein step c) is performed for 20 to 60 hours.

7. The process of claim 6, wherein step c) is performed for about 24-48 hours.

8. The process of claim 1, wherein the total time to perform step b) and step c) is 72 to 150 hours.

9. The process of claim 1, wherein step b) is performed at a temperature of about 55° C.

10. The process of claim 1, wherein step b) is performed at a temperature of about 60° C.

11. The process of claim 1, wherein step b) is performed at a temperature of about 65° C.

12. The process of claim 1, wherein the dry matter content of said corn fiber, corn stover or wheat straw in step b) is about 14-25%.

13. The process of claim 1, wherein the filamentous fungal strain is from the genus *Penicillium* or *Talaromyces*.

14. The process of claim 13, wherein the filamentous fungal strain is *Talaromyces emersonii*.

15. The process of claim 1, wherein step c) is performed under oxygen-limited conditions.

16. The process of claim 1, wherein the biofuel is ethanol or butanol.

17. The process of claim 16, wherein the biofuel is ethanol.

18. The process of claim 1, wherein step b) results in a release of 90% of available sugar in the corn fiber, corn stover or wheat straw.

* * * * *